(12) United States Patent
MacDonald et al.

(10) Patent No.: US 10,583,198 B2
(45) Date of Patent: *Mar. 10, 2020

(54) DOSING STRATEGIES FOR TARGETING EPCAM POSITIVE BLADDER CANCER

(71) Applicant: VIVENTIA BIO INC., Winnipeg, Manitoba (CA)

(72) Inventors: Glen MacDonald, Winnipeg (CA); Stephen Hurly, Haddonfield, NJ (US)

(73) Assignee: VIVENTIA BIO INC., Winnipeg, MB (CA)

( * ) Notice: Subject to any disclaimer, the term of this patent is extended or adjusted under 35 U.S.C. 154(b) by 0 days.

This patent is subject to a terminal disclaimer.

(21) Appl. No.: 15/557,369

(22) PCT Filed: Mar. 11, 2016

(86) PCT No.: PCT/US2016/022085
§ 371 (c)(1),
(2) Date: Sep. 11, 2017

(87) PCT Pub. No.: WO2016/145354
PCT Pub. Date: Sep. 15, 2016

(65) Prior Publication Data
US 2018/0104355 A1 Apr. 19, 2018

Related U.S. Application Data

(60) Provisional application No. 62/267,386, filed on Dec. 15, 2015, provisional application No. 62/132,251, filed on Mar. 12, 2015.

(51) Int. Cl.
*A61K 39/395* (2006.01)
*A61K 47/68* (2017.01)
*C07K 16/30* (2006.01)
*A61P 35/00* (2006.01)
*A61K 33/24* (2019.01)
*A61K 31/282* (2006.01)
*A61K 31/337* (2006.01)
*A61K 31/513* (2006.01)
*A61K 38/14* (2006.01)
*A61K 31/519* (2006.01)
*A61K 31/664* (2006.01)
*C07K 16/28* (2006.01)
*A61K 38/16* (2006.01)
*A61K 38/45* (2006.01)
*A61K 31/555* (2006.01)
*A61K 31/675* (2006.01)
*A61K 45/06* (2006.01)
*A61K 39/00* (2006.01)

(52) U.S. Cl.
CPC ........ *A61K 47/6861* (2017.08); *A61K 31/282* (2013.01); *A61K 31/337* (2013.01); *A61K 31/513* (2013.01); *A61K 31/519* (2013.01); *A61K 31/555* (2013.01); *A61K 31/664* (2013.01); *A61K 31/675* (2013.01); *A61K 33/24* (2013.01); *A61K 38/14* (2013.01); *A61K 38/164* (2013.01); *A61K 38/45* (2013.01); *A61K 39/39558* (2013.01); *A61K 45/06* (2013.01); *A61K 47/6829* (2017.08); *A61K 47/6849* (2017.08); *A61P 35/00* (2018.01); *C07K 16/2863* (2013.01); *C07K 16/3038* (2013.01); *C12Y 204/02036* (2013.01); *A61K 2039/505* (2013.01); *A61K 2039/54* (2013.01); *A61K 2039/545* (2013.01); *C07K 2317/622* (2013.01)

(58) Field of Classification Search
None
See application file for complete search history.

(56) References Cited

U.S. PATENT DOCUMENTS

| 5,082,767 | A | 1/1992 | Hatfield et al. |
| 5,690,928 | A | 11/1997 | Heimbrook et al. |
| 6,339,070 | B1 | 1/2002 | Emery et al. |
| 7,033,798 | B2 | 4/2006 | Pluckthun et al. |
| 7,339,031 | B2 | 3/2008 | Baker et al. |
| 7,341,722 | B2 | 3/2008 | Pluckthun et al. |
| 7,655,437 | B2 | 2/2010 | Jevsevar et al. |
| 7,858,088 | B2 | 12/2010 | Pluckthun et al. |
| 8,137,932 | B2 | 3/2012 | Pluckthun et al. |
| 8,263,744 | B2 | 9/2012 | Cizeau et al. |
| 8,318,472 | B2 | 11/2012 | Cizeau et al. |

(Continued)

FOREIGN PATENT DOCUMENTS

| CA | 2424255 A1 | 9/2004 |
| CA | 2560278 A1 | 9/2005 |

(Continued)

OTHER PUBLICATIONS

Brown et al (J. Immunol. May 1996; 156(9):3285-3291 (Year: 1996).*
Al-Lazikani, B., et al., "Standard conformations for the canonical structures of immunoglobulins." J Mol Biol. (1997); 273 (4): 927-948.
Anonymous: "History of Changes for Study: NCT02449239 Vicinium Treatment for Subjects With Non-muscle Invasive Bladder Cancer Previously Treated With BCG.", clinicaltrials.gov, Oct. 19, 2015 (Oct. 19, 2015), pp. 1-9, XP055494827, Retrieved from the Internet: URL:https://clinicaltrials.gov/ct2/history/NCT02449239?V8=View#StudyPageTop [retrieved on Jul. 24, 2018], 9 pages.

(Continued)

*Primary Examiner* — Sheela J. Huff
(74) *Attorney, Agent, or Firm* — Hogan Lovells US LLP

(57) ABSTRACT

The present disclosure provides methods for treatment of bladder cancer. The methods include administering an immunoconjugate to a subject in a dosing regimen that includes an induction phase with twice weekly followed by once weekly dosing, and optionally a maintenance phase. The immunoconjugates useful in the methods provided include immunoconjugates having a binding protein that specifically binds to Ep-CAM and a toxin molecule.

17 Claims, 1 Drawing Sheet
Specification includes a Sequence Listing.

(56) References Cited

U.S. PATENT DOCUMENTS

| | | | |
|---|---|---|---|
| 8,545,840 | B2 | 10/2013 | Zangemeister-Wittke et al. |
| 9,259,484 | B2 | 2/2016 | Zangemeister-Wittke et al. |
| 9,822,182 | B2 | 11/2017 | Cizeau et al. |
| 2002/0146846 | A1 | 10/2002 | Pluckthun et al. |
| 2002/0193570 | A1 | 12/2002 | Gillies et al. |
| 2003/0148950 | A1 | 8/2003 | Xin et al. |
| 2004/0022726 | A1 | 2/2004 | Goldenberg et al. |
| 2005/0136049 | A1 | 6/2005 | Ledbetter et al. |
| 2007/0196366 | A1 | 8/2007 | Zangemeister-Wittke et al. |
| 2009/0081191 | A1 | 3/2009 | Kufer et al. |
| 2009/0171317 | A1 | 7/2009 | Versi |
| 2010/0215670 | A1 | 8/2010 | Cizeau et al. |
| 2010/0249039 | A1 | 9/2010 | Zangemeister-Wittke et al. |
| 2010/0310463 | A1 | 12/2010 | Gunnarsson et al. |
| 2011/0104062 | A1 | 5/2011 | Siu et al. |
| 2014/0178417 | A1 | 6/2014 | Zangemeister-Wittke et al. |
| 2014/0193436 | A1 | 7/2014 | Prudent et al. |
| 2016/0060352 | A1 | 3/2016 | Tanaka et al. |
| 2016/0199507 | A1 | 7/2016 | Zangemeister-Wittke et al. |
| 2016/0237164 | A1 | 8/2016 | Cizeau et al. |
| 2018/0104356 | A1 | 4/2018 | MacDonald et al. |

FOREIGN PATENT DOCUMENTS

| | | |
|---|---|---|
| WO | WO 1998/055623 A1 | 12/1998 |
| WO | WO 1999/065521 A1 | 12/1999 |
| WO | WO 2000/061635 A2 | 10/2000 |
| WO | WO 2000/069914 A2 | 11/2000 |
| WO | WO 2002/090566 A2 | 11/2002 |
| WO | WO 2003/033654 A2 | 4/2003 |
| WO | WO 2004/096271 A1 | 11/2004 |
| WO | WO 2005/090579 A1 | 9/2005 |
| WO | WO 2005/121341 A1 | 12/2005 |
| WO | WO 2008/128330 A1 | 10/2008 |
| WO | WO 2009/039630 A1 | 4/2009 |
| WO | WO 2010/115630 A1 | 10/2010 |
| WO | WO 2011/116387 A1 | 9/2011 |
| WO | WO 2014/166002 A1 | 10/2014 |
| WO | WO 2015/048901 A1 | 4/2015 |
| WO | WO 2016/145349 A1 | 9/2016 |
| WO | WO 2016/145354 A1 | 9/2016 |
| WO | WO 2017/040801 A2 | 3/2017 |

OTHER PUBLICATIONS

Apantaku, L.M., "Breast cancer diagnosis and screening." American Family Physician (2000); 62.3: 9 pages.

Azemar, et al., "Recombinant antibody toxins specific for ErbB2 and EGF receptor inhibit the in vitro growth of human head and neck cancer cells and cause rapid tumor regression in vivo." International Journal of Cancer (20002); 86.2: 269-275.

Balzar, et al., "The biology of the 17-1A antigen (Ep-CAM)." Journal of Molecular Medicine (1999); 77.10: 699-712.

Battelli, et al., "Toxicity of ribosome-inactivating proteins-containing immunotoxins to a human bladder carcinoma cell line." Int J Cancer (1996); 65(4): 485-490.

Bothmann and Plückthun, "Selection for a periplasmic factor improving phage display and functional periplasmic expression." Nat Biotechnol. (1998); 16(4): 376-380.

Breuhahn, et al., "Expression of epithelial cellular adhesion molecule (Ep-CAM) in chronic (necro-) inflammatory liver diseases and hepatocellular carcinoma." Hepatology Research (2006); 34.1: 50-56.

Carter and Merchant, "Engineering antibodies for imaging and therapy." Curr Opin Biotechnol. (1997); 8(4): 449-454.

Carter, P., et al., "Humanization of an anti-p185HER2 antibody for human cancer therapy." Proc Natl Acad Sci U S A. (1992); 89(10): 4285-4289.

Casset, et al., "A peptide mimetic of an anti-CD4 monoclonal antibody by rational design." Biochem Biophys Res Commun. (2003); 307(1): 198-205.

Chatterjee, M.B., et al., "Idiotypic antibody immunotherapy of cancer." Cancer Immunol Immunother. Feb. 1994;38 (2):75-82.

Chaubal, et al., "Ep-CAM—a marker for the detection of disseminated tumor cells in patients suffering from SCCHN." Anticancer Research (1999); 19(3B): 2237-2242.

Chen, et al., "Selection and analysis of an optimized anti-VEGF antibody: crystal structure of an affinity-matured fab in complex with antigen." J Mol Biol. (1999); 293(4): 865-881.

Colombo, Federico, et al., "Evidence of distinct tumour-propagating cell populations with different properties in primary human hepatocellular carcinoma." PLoS One (2011); 6.6: e21369.

De Pascalis, et al., "Grafting of "abbreviated" complementarity-determining regions containing specificity-determining residues essential for ligand contact to engineer a less immunogenic humanized monoclonal antibody." J. Immunol. (2002); 169(6): 3076-3084.

Dermer, G.B., "Another Anniversary for the war on Cancer." Bio/Technology (1994); 12: 320.

Di Paolo, et al., "A recombinant immunotoxin derived from a humanized epithelial cell adhesion molecule-specific single-chain antibody fragment has potent and selective antitumor activity." Clin Cancer Res. (2003); 9(7): 2837-2848.

Dickstein, et al., "LBA27 Phase 3 Study of Vicinium in BCG-Unresponsive Non-Muscle Invasive Bladder Cancer: Initial Results." The Journal of Urology (2018); 199 (4): Supplement, e1167, 1 page.

Eigenbrot, C., et al., "X-ray structures of the antigen-binding domains from three variants of humanized antip-185HER2 antibody 4D5 and comparison with molecular modeling." J Mol Biol. (1993); 229(4): 969-995.

Entwistle, Joycelyn, et al., "Preclinical evaluation of VB6-845: an anti-EpCAM immunotoxin with reduced immunogenic potential." Cancer Biotherapy and Radiopharmaceuticals (2012); 27.9: 582-592.

European Patent Application No. 10011667.2, Extended European Search Report dated Sep. 29, 2011, 9 pages.

European Patent Application No. 14172801.4, Extended European Search Report dated Jan. 8, 2015, 11 pages.

European Patent Application No. 14782607.7, Extended European Search Report dated Nov. 16, 2016, 12 pages.

European Patent Application No. 14850812.0, Extended European Search Report dated Feb. 27, 2017, 9 pages.

European Patent Application No. 16762631.6, Extended European Search Report dated Aug. 6, 2018, 11 pages.

Gherardi, et al., "Structural basis of haptocyte growth factor/scatter factor and MET signalling." Proc. Nat. Acad. Sci. USA (2006); 103(11): 4046-4051.

Gibson, A.L., et al., "Differences in crystal properties and ligand affinities of an antifluorescyl Fab (4-4-20) in two solvent systems." Proteins (1988); 3(3):155-160.

Glockshuber, R., et al., "A comparison of strategies to stabilize immunoglobulin Fv-fragments." Biochemistry (1990); 29(6): 1362-1367.

Gura, T., "Systems for identifying new drugs are often faulty." Science (1997); 278(5340): 1041-1042.

Helfrich, W., et al. "Construction and characterization of a bispecific diabody for retargeting T cells to human carcinomas." Int J Cancer (1998); 76(2): 232-239.

Holm, et al., "Functional mapping and single chain construction of the anti-cytokeratin 8 monoclonal antibody TS1." Mol Immunol. (2007); 44(6): 1075-1084. Epub Sep. 20, 2006.

International Patent Application No. PCT/EP/2000/003176, International Search Report dated Jan. 29, 2001, 3 pages.

International Patent Application No. PCT/CA2004/000637, International preliminary Report on Patentability dated Nov. 4, 2005, 10 pages.

International Patent Application No. PCT/CA2004/000637, International Search Report and Written Opinion dated Oct. 28, 2004, 15 pages.

International Patent Application No. PCT/CA2008/000711, International Preliminary Report on Patentability dated Oct. 20, 2009, 8 pages.

International Patent Application No. PCT/CA2008/000711, International Search Report and Written Opinion dated Aug. 8, 2008, 13 pages.

(56) References Cited

OTHER PUBLICATIONS

International Patent Application No. PCT/CA2008/001680, International Preliminary Report on Patentability dated Mar. 30, 2010, 8 pages.
International Patent Application No. PCT/CA2008/001680, International Search Report and Written Opinion dated Jan. 29, 2009, 11 pages.
International Patent Application No. PCT/CA2014/050373, International Search Preliminary Report on Patentability dated Oct. 13, 2015, 8 pages.
International Patent Application No. PCT/CA2014/050373, International Search Report and Written Opinion dated Jul. 11, 2014, 15 pages.
International Patent Application No. PCT/CA2014/050950, International Preliminary Report on Patentability dated Apr. 5, 2016, 9 pages.
International Patent Application No. PCT/CA2014/050950, International Search Report and Written Opinion dated Jan. 2, 2015, 15 pages.
International Patent Application No. PCT/US2016/022077, International Search Report and Written Opinion dated Jun. 10, 2016, 21 pages.
International Patent Application No. PCT/US2016/022077, International Preliminary Report on Patentability dated Sep. 12, 2017, 17 pages.
International Patent Application No. PCT/US2016/022085, International Search Report and Written Opinion dated Jun. 10, 2016, 20 pages.
International Patent Application No. PCT/US2016/022085, International Preliminary Report on Patentability dated Sep. 12, 2017, 15 pages.
International Patent Application No. PCT/US2016/049932, International Search Report and Written Opinion dated Mar. 23, 2017, 12 pages.
Jain, R.K., et al., "Barriers to drug delivery in solid tumors." Sci Am. (1994); 271(1): 58-65.
Jones, Tim D., et al., "Deimmunization of Monoclonal Antibodies." Methods in Molecular Biology (2009); Chapter 21, 525: 405-423.
Jung and Plückthun, "Improving in vivo folding and stability of a single-chain Fv antibody fragment by loop grafting." Protein Eng. (1997); 10(8): 959-966.
Kehoe and Capra, "Sequence relationships among the variable regions of immunoglobulin heavy chains from various mammalian species." PNAS USA (1972); 69(8): 2052-2055.
Kimura, et al., "Characterization of the epithelial cell adhesion molecule (EpCAM)+ cell population in hepatocellular carcinoma cell lines." Cancer Science (2010); 101.10: 2145-2155.
Knappik and Plückthun, "Engineered turns of a recombinant antibody improve its in vivo folding." Protein Eng. (1995); 8 (1): 81-89.
Kowalski, et al., "A Phase I study of an intravesically administered immunotoxin targeting EpCAM for the treatment of nonmuscle-invasive bladder cancer in BCGrefractory and BCG-intolerant patients." Drug Des Devel Ther (2010); 4: 313-320.
Kowalski, et al., "A phase II study of oportuzumab monatox: an immunotoxin therapy for patients with noninvasive urothelial carcinoma in situ previously treated with bacillus Calmette-Guerin." The Journal of Urology (2012); 188.5: 1712-1718.
Krebber, A., et al. "Reliable cloning of functional antibody variable domains from hybridomas and spleen cell repertoires employing a reengineered phage display system." J Immunol Methods. (1997); 201(1): 35-55.
Kreitman, "Immunotoxins in cancer therapy." Curr Opin Immunol. (1999); 11(5): 570-578.
Kubetzko and Zangemeister-Wittke, "Engineering of an EGP-2 (Ep-CAM) specific antibody-immunotoxin for targeted therapy of solid tumors." Swiss Cancer Bulletin (2000); 20(4): 182-187.
Langedijk, A.C., et al., "The nature of antibody heavy chain residue H6 strongly influences the stability of a VH domain lacking the disulfide bridge." J Mol Biol. (1998); 283(1): 95-110.
LeMaistre, et al., "An immunotoxin cytotoxic for breast cancer cells in vitro." Cancer Res. (1987); 47(3): 730-734.
Ma, Tianzhong, et al., "Human papillomavirus type 18 E6 and E7 genes integrate into human hepatoma derived cell line Hep G2." PloS One (2012); 7.5: e37964, pp. 1-9.
MacCallum, et al., "Antibody-antigen interactions: contact analysis and binding site topography." J Mol Biol. (1996); 262(5): 732-745.
Martin and Weber, "Genetic and hormonal risk factors in breast cancer." J Natl Cancer Inst. (2000); 92(14): 1126-1135.
McKiernan, et al., "Phase I trial of intravesical docetaxel in the management of superficial bladder cancer refractory to standard intravesical therapy." Journal of Clinical Oncology (2006); 24.19: 3075-3080.
McLaughlin, et al., "The epithelial glycoprotein 2 (EGP-2) promoter-driven epithelial-specific expression of EGP-2 in transgenic mice: a new model to study carcinoma-directed immunotherapy." Cancer Res. (2001); 61(10): 4105-4111.
Mueller, et al., "Expression of tissue factor by melanoma cells promotes efficient hematogenous metastasis." Proc Natl Acad Sci USA (1992); 89(24): 11832-11836.
Ogawa, et al., "EpCAM-targeted therapy for human hepatocellular carcinoma." Annals of Surgical Oncology (2014); 21.4: 1314-1322.
Oishi and Wang, "Novel therapeutic strategies for targeting liver cancer stem cells." Int J Biol Sci (2011); 7.5: 517-535.
Öelschläger, et al., "Identification of factors impeding the production of a single-chain antibody fragment in *Escherichia coli* by comparing in vivo and in vitro expression." Applied Microbiology and Biotechnology (2003); 61.2: 123-132.
Pang and Poon, "Cancer stem cell as a potential therapeutic target in hepatocellular carcinoma." Current Cancer Drug Targets (2012); 12.9: 1081-1094.
Parker, et al., "Optimization algorithms for functional deimmunization of therapeutic proteins." BMC Bioinformatics (2010); 11: 180, 15 pages.
Plückthun and Pack, "New protein engineering approaches to multivalent and bispecific antibody fragments." Immunotechnology (1997); 3(2): 83-105.
Proba, K., et al., "Antibody scFv fragments without disulfide bonds made by molecular evolution." J Mol Biol. (1998); 275(2): 245-253.
Rudikoff, et al., "Single amino acid substitution altering antigen-binding specificity." Proc Natl Acad Sci USA (1982); 79(6): 1979-1983.
Saul, F.A., "Structural implications of VH sequence patterns." 55th Forum in Immunology, A Structural view of immune recognition by antibodies. Research in Immunology (1994); 145.1: 61-66.
Saul and Poljak, "Structural patterns at residue positions 9, 18, 67 and 82 in the VH framework regions of human and murine immunoglobulins." J Mol Biol. Mar. 5, 1993;230(1):15-20.
Schumann, et al., "Importance of Kupffer Cells for T-Cell-Dependent Liver Injury in Mice," American Journal of Pathology, 157(5):1672-1683 (2000).
Schumann, et al., "Acute Hepatotoxicity of Pseudomonas aeruginosa Exotoxin A in Mice Depends on T Cells and TNF," Journal of Immunology, 1661:5745-5754 (1998).
Seaver, "Monoclonal Antibodies in Industry: More Difficult Than Originally Thought." Genetic Engineering News (1994); 14(14): 10 and 21.
Shan, et al., "Angiogenesis and clinicopathologic characteristics in different hepatocellular carcinoma subtypes defined by EpCAM and α-fetoprotein expression status." Medical Oncology (2011); 28.4: 1012-1016.
Simon, et al., "Epithelial cell adhesion molecule-targeted drug delivery for cancer therapy." Expert Opinion on Drug Delivery (2013); 10.4: 451-468.
Starling, et al., "In vivo efficacy of monoclonal antibody-drug conjugates of three different sub isotypes which bind the human tumor-associated antigen defined by the KS1/4 monoclonal antibody." Cancer Immunol Immunother. (1989); 28(3): 171-178.
Stratagen Catalog (1988)(pp. 1-2).
Strome, et al., "Interleukin 4 Receptor-directed Cytotoxin Therapy for Human Head and Neck Squamous Cell Carcinoma in Animal Models." Clin Cancer Res. (2002); 8(1): 281-286.

(56) References Cited

OTHER PUBLICATIONS

Syrigos, et al., "Use of monoclonal antibodies for the diagnosis and treatment of bladder cancer." Hybridoma (1999); 18(3): 219-224.

Thiesen, et al., "Selective killing of human bladder cancer cells by combined treatment with A and B chain ricin antibody conjugates." Cancer Res. (1987); 47(2): 419-423.

Thurber and Weissleder, "Quantitating Antibody Uptake in Vivo: Conditional Dependence on Antigen Expression Levels." Mol Imaging Biol. (2011); 13 (4): 623-632.

Vajdos, et al., "Comprehensive functional maps of antigen-binding site of an anti-ErbB2 antibody obtained with shotgun scanning mutagenesis." J Mol Biol. (2002); 320(2): 415-428.

Velders, et al., "The impact of antigen density and antibody affinity of antibody-dependent cellular cytotoxicity: relevance for immunotherapy of carcinomas." Br J Cancer (1998); 78(4): 478-483.

Wahl, Kristin, et al., "Increased apoptosis induction in hepatocellular carcinoma by a novel tumor-targeted TRAIL fusion protein combined with bortezomib." Hepatology (2013); 57.2: 625-636.

Waibel, R., et al., "Stable one-step technetium-99m labeling of His-tagged recombinant proteins with a novel Tc(I)-carbonyl complex." Nat Biotechnol. (1999); 17(9): 897-901.

Wawrzynczak, et al., "Pharmacokinetics in the rat of a panel of immunotoxins made with abrin A chain, ricin A chain, gelonin, and momordin." Cancer Res. (1990); 50(23): 7519-7526.

Willuda, et al., "High thermal stability is essential for tumor targeting of antibody fragments: engineering of a humanized anti-epithelial glycoprotein-2 (epithelial cell adhesion molecule) single-chain Fv fragment." Cancer Res. (1999); 59(22): 5758-5767.

Willuda, J., et al., "Rational engineering for high stability is required for tumor targeting of a high-affinity scFv fragment specific for the panepithelial glycoprotein egp-2." Proceedings of the American Association for Cancer Research Annual Meeting (Mar. 1999), vol. 40, O.354, Abst. 2343, Meeting Info,: 90th Annual Meeting of the American Association for Cancer Research, Philadelphia, PA, USA, Apr. 10-14, 1999.

Winter, et al., "The Epithelial Cell Adhesion Molecule (Ep-CAM) as a Morphoregulatory Molecule Is a Tool in Surgical Pathology." Am J Pathol. (2003); 163(6): 2139-2148.

Wörn and Plückthun, "An intrinsically stable antibody scFv fragment can tolerate the loss of both disulfide bonds and fold correctly." FEBS Lett. (1998); 427 (3): 357-361.

Wu, et al., "Humanization of murine monoclonal antibody by simultaneous optimization of framework and CDR residues." J Mol Biol. (1999); 294(1): 151-162.

Yamashita, et al., "EpCAM-positive hepatocellular carcinoma cells are tumor-initiating cells with stem/progenitor cell features." Gastroenterology (2009); 136.3: 1012-1024.

Zimmermann, et al., "A novel immunotoxin recognising the epithelial glycoprotein-2 has potent antitumoural activity on chemotherapy-resistant lung cancer." Cancer Immunol Immunother. (1997); 44(1): 1-9.

Zorzos, et al., "Expression of a cell surface antigen recognized by the monoclonal antibody AUA1 in bladder carcinoma: an immunohistochemical study." European Urology (1994); 28.3: 251-254.

\* cited by examiner

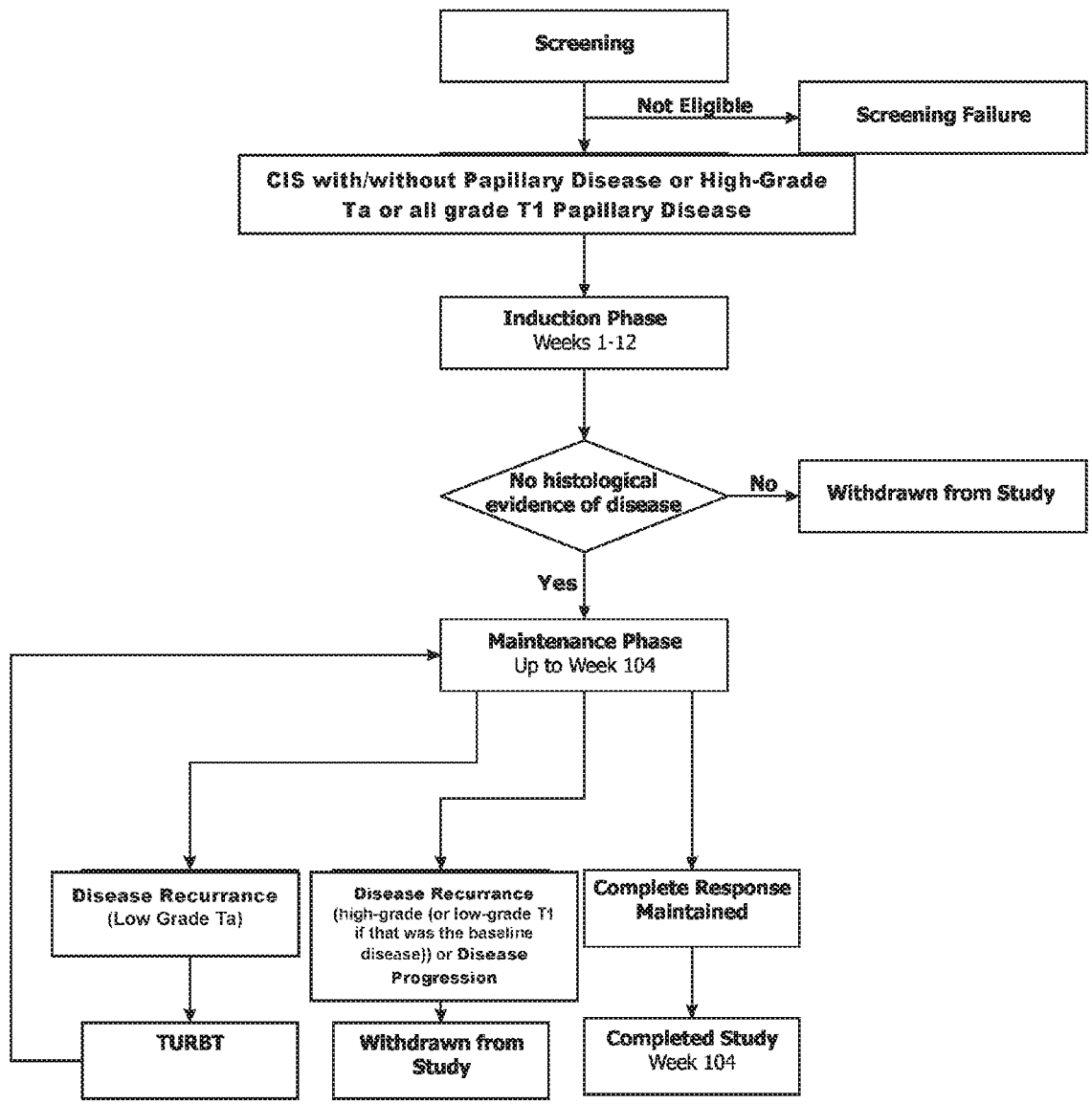

SEQUENCE LISTING

```
<160> NUMBER OF SEQ ID NOS: 14

<210> SEQ ID NO 1
<211> LENGTH: 2084
<212> TYPE: DNA
<213> ORGANISM: Artificial Sequence
<220> FEATURE:
<223> OTHER INFORMATION: VB4-845
<220> FEATURE:
<221> NAME/KEY: CDS
<222> LOCATION: (66)..(2084)

<400> SEQUENCE: 1
gaattcctgc aggtctatgg aacgataaat gcccatgaaa attctatttc aaggagacag        60 tcata atg aaa tac cta ttg cct acg gca gcc gct gga ttg tta tta ctc       110
      Met Lys Tyr Leu Leu Pro Thr Ala Ala Ala Gly Leu Leu Leu Leu
      1               5                   10                  15 gct gcc caa cca gcg atg gcg cac cat cat cac cat cac gat atc cag         158
Ala Ala Gln Pro Ala Met Ala His His His His His His Asp Ile Gln
                20                  25                  30 atg acc cag tcc ccg tcc tcc ctg agt gct tct gtt ggt gac cgt gtt         206
Met Thr Gln Ser Pro Ser Ser Leu Ser Ala Ser Val Gly Asp Arg Val
            35                  40                  45 acc atc acc tgc cgt tcc acc aaa tcc ctc ctg cac tcc aac ggt atc         254
Thr Ile Thr Cys Arg Ser Thr Lys Ser Leu Leu His Ser Asn Gly Ile
        50                  55                  60 acc tac ctt tat tgg tat caa cag aaa ccg ggt aaa gct ccg aaa ctt         302
Thr Tyr Leu Tyr Trp Tyr Gln Gln Lys Pro Gly Lys Ala Pro Lys Leu
    65                  70                  75 ctg atc tac cag atg tcc aac ctg gct tcc ggt gtt ccg tct cgt ttc         350
Leu Ile Tyr Gln Met Ser Asn Leu Ala Ser Gly Val Pro Ser Arg Phe
80                  85                  90                  95 tcc agt tct ggt tct ggt acc gac ttc acc ctg acc atc tct tct ctg         398
Ser Ser Ser Gly Ser Gly Thr Asp Phe Thr Leu Thr Ile Ser Ser Leu
                100                 105                 110 cag ccg gaa gac ttc gct acc tac tac tgc gct cag aac ctg gaa atc         446
Gln Pro Glu Asp Phe Ala Thr Tyr Tyr Cys Ala Gln Asn Leu Glu Ile
            115                 120                 125 ccg cgt acc ttc ggt cag ggt acc aaa gtt gaa ctt aag cgc gct acc         494
Pro Arg Thr Phe Gly Gln Gly Thr Lys Val Glu Leu Lys Arg Ala Thr
        130                 135                 140 ccg tct cac aac tcc cac cag gtt cca tcc gca ggc ggt ccg act gct         542
Pro Ser His Asn Ser His Gln Val Pro Ser Ala Gly Gly Pro Thr Ala
    145                 150                 155 aac tct gga act agt gga tcc gaa gta cag ctg gtt cag tcc ggc ccg         590
Asn Ser Gly Thr Ser Gly Ser Glu Val Gln Leu Val Gln Ser Gly Pro
160                 165                 170                 175 ggt ctt gtt caa ccg ggt ggt tcc gtt cgt atc tct tgc gct gct tct         638
Gly Leu Val Gln Pro Gly Gly Ser Val Arg Ile Ser Cys Ala Ala Ser
                180                 185                 190 ggt tac acg ttc acc aac tac ggc atg aac tgg gtc aaa cag gct ccg         686
```

|     |     |     |     |     |     |     |     |     |     |     |     |     |
|---|---|---|---|---|---|---|---|---|---|---|---|---|
| Gly | Tyr | Thr | Phe | Thr | Asn | Tyr | Gly | Met | Asn | Trp | Val | Lys | Gln | Ala | Pro |
|     |     |     | 195 |     |     |     | 200 |     |     |     |     | 205 |     |     |     |

```
ggt aaa ggc ctg gaa tgg atg ggc tgg atc aac acc tac acc ggt gaa      734
Gly Lys Gly Leu Glu Trp Met Gly Trp Ile Asn Thr Tyr Thr Gly Glu
        210                 215                 220 tcc acc tac gct gac tcc ttc aaa ggt cgc ttc act ttc tcc ctc gac      782
Ser Thr Tyr Ala Asp Ser Phe Lys Gly Arg Phe Thr Phe Ser Leu Asp
225                 230                 235 aca agt gct agt gct gca tac ctc caa atc aac tcg ctg cgt gca gag      830
Thr Ser Ala Ser Ala Ala Tyr Leu Gln Ile Asn Ser Leu Arg Ala Glu
240                 245                 250                 255 gat aca gca gtc tat tac tgc gcc cgt ttc gct atc aaa ggt gac tac      878
Asp Thr Ala Val Tyr Tyr Cys Ala Arg Phe Ala Ile Lys Gly Asp Tyr
                260                 265                 270 tgg ggt caa ggc acg ctg ctg acc gtt tcc tcg gaa ttt ggt ggc gcg      926
Trp Gly Gln Gly Thr Leu Leu Thr Val Ser Ser Glu Phe Gly Gly Ala
                275                 280                 285 ccg gag ttc ccg aaa ccg tcc acc ccg ccg ggt tct tct ggt tta gag      974
Pro Glu Phe Pro Lys Pro Ser Thr Pro Pro Gly Ser Ser Gly Leu Glu
            290                 295                 300 ggc ggc agc ctg gcc gcg ctg acc gcg cac cag gcc tgc cac ctg ccg     1022
Gly Gly Ser Leu Ala Ala Leu Thr Ala His Gln Ala Cys His Leu Pro
        305                 310                 315 ctg gag act ttc acc cgt cat cgc cag ccg cgc ggc tgg gaa caa ctg     1070
Leu Glu Thr Phe Thr Arg His Arg Gln Pro Arg Gly Trp Glu Gln Leu
320                 325                 330                 335 gag cag tgc ggc tat ccg gtg cag cgg ctg gtc gcc ctc tac ctg gcg     1118
Glu Gln Cys Gly Tyr Pro Val Gln Arg Leu Val Ala Leu Tyr Leu Ala
                340                 345                 350 gcg cga ctg tca tgg aac cag gtc gac cag gtg atc cgc aac gcc ctg     1166
Ala Arg Leu Ser Trp Asn Gln Val Asp Gln Val Ile Arg Asn Ala Leu
                355                 360                 365 gcc agc ccc ggc agc ggc ggc gac ctg ggc gaa gcg atc cgc gag cag     1214
Ala Ser Pro Gly Ser Gly Gly Asp Leu Gly Glu Ala Ile Arg Glu Gln
        370                 375                 380 ccg gag cag gcc cgt ctg gcc ctg acc ctg gcc gcc gcc gag agc gag     1262
Pro Glu Gln Ala Arg Leu Ala Leu Thr Leu Ala Ala Ala Glu Ser Glu
385                 390                 395 cgc ttc gtc cgg cag ggc acc ggc aac gac gag gcc ggc gcg gcc agc     1310
Arg Phe Val Arg Gln Gly Thr Gly Asn Asp Glu Ala Gly Ala Ala Ser
400                 405                 410                 415 gcc gac gtg gtg agc ctg acc tgc ccg gtc gcc gcc ggt gaa tgc gcg     1358
Ala Asp Val Val Ser Leu Thr Cys Pro Val Ala Ala Gly Glu Cys Ala
                420                 425                 430 ggc ccg gcg gac agc ggc gac gcc ctg ctg gag cgc aac tat ccc act     1406
Gly Pro Ala Asp Ser Gly Asp Ala Leu Leu Glu Arg Asn Tyr Pro Thr
                435                 440                 445 ggc gcg gag ttc ctc ggc gac ggt ggc gac gtc agc ttc agc acc cgc     1454
Gly Ala Glu Phe Leu Gly Asp Gly Gly Asp Val Ser Phe Ser Thr Arg
        450                 455                 460 ggc acg cag aac tgg acg gtg gag cgg ctg ctc cag gcg cac cgc caa     1502
Gly Thr Gln Asn Trp Thr Val Glu Arg Leu Leu Gln Ala His Arg Gln
465                 470                 475 ctg gag gag cgc ggc tat gtg ttc gtc ggc tac cac ggc acc ttc ctc     1550
Leu Glu Glu Arg Gly Tyr Val Phe Val Gly Tyr His Gly Thr Phe Leu
480                 485                 490                 495 gaa gcg gcg caa agc atc gtc ttc ggg ggg gtg cgc gcg cgc agc cag     1598
Glu Ala Ala Gln Ser Ile Val Phe Gly Gly Val Arg Ala Arg Ser Gln
                500                 505                 510
```

| | | |
|---|---|---|
| gat ctc gac gcg atc tgg cgc ggt ttc tat atc gcc ggc gat ccg gcg<br>Asp Leu Asp Ala Ile Trp Arg Gly Phe Tyr Ile Ala Gly Asp Pro Ala<br>515 520 525 | | 1646 |
| ctg gcc tac ggc tac gcc cag gac cag gaa ccc gac gcg cgc ggc cgg<br>Leu Ala Tyr Gly Tyr Ala Gln Asp Gln Glu Pro Asp Ala Arg Gly Arg<br>530 535 540 | | 1694 |
| atc cgc aac ggt gcc ctg ctg cgg gtc tat gtg ccg cgc tcc agc ctg<br>Ile Arg Asn Gly Ala Leu Leu Arg Val Tyr Val Pro Arg Ser Ser Leu<br>545 550 555 | | 1742 |
| ccg ggc ttc tac cgc acc ggc ctg acc ctg gcc gcg ccg gag gcg gcg<br>Pro Gly Phe Tyr Arg Thr Gly Leu Thr Leu Ala Ala Pro Glu Ala Ala<br>560 565 570 575 | | 1790 |
| ggc gag gtc gaa cgg ctg atc ggc cat ccg ctg ccg ctg cgc ctg gac<br>Gly Glu Val Glu Arg Leu Ile Gly His Pro Leu Pro Leu Arg Leu Asp<br>580 585 590 | | 1838 |
| gcc atc acc ggc ccc gag gag gaa ggc ggg cgc ctg gag acc att ctc<br>Ala Ile Thr Gly Pro Glu Glu Glu Gly Gly Arg Leu Glu Thr Ile Leu<br>595 600 605 | | 1886 |
| ggc tgg ccg ctg gcc gag cgc acc gtg gtg att ccc tcg gcg atc ccc<br>Gly Trp Pro Leu Ala Glu Arg Thr Val Val Ile Pro Ser Ala Ile Pro<br>610 615 620 | | 1934 |
| acc gac ccg cgc aac gtc ggt ggc gac ctc gac ccg tcc agc atc ccc<br>Thr Asp Pro Arg Asn Val Gly Gly Asp Leu Asp Pro Ser Ser Ile Pro<br>625 630 635 | | 1982 |
| gac aag gaa cag gcg atc agc gcc ctg ccg gac tac gcc agc cag ccc<br>Asp Lys Glu Gln Ala Ile Ser Ala Leu Pro Asp Tyr Ala Ser Gln Pro<br>640 645 650 655 | | 2030 |
| ggc aaa ccg ccg cat cac cac cat cac cat aaa gac gaa ctg tag tga<br>Gly Lys Pro Pro His His His His His His Lys Asp Glu Leu<br>660 665 | | 2078 |
| ctc gag<br>Leu Glu<br>670 | | 2084 |

```
<210> SEQ ID NO 2
<211> LENGTH: 669
<212> TYPE: PRT
<213> ORGANISM: Artificial Sequence
<220> FEATURE:
<223> OTHER INFORMATION: Synthetic Construct

<400> SEQUENCE: 2
```

Met Lys Tyr Leu Leu Pro Thr Ala Ala Ala Gly Leu Leu Leu Leu Ala
1               5                   10                  15

Ala Gln Pro Ala Met Ala His His His His His Asp Ile Gln Met
                20                  25                  30

Thr Gln Ser Pro Ser Ser Leu Ser Ala Ser Val Gly Asp Arg Val Thr
            35                  40                  45

Ile Thr Cys Arg Ser Thr Lys Ser Leu Leu His Ser Asn Gly Ile Thr
        50                  55                  60

Tyr Leu Tyr Trp Tyr Gln Gln Lys Pro Gly Lys Ala Pro Lys Leu Leu
65                  70                  75                  80

Ile Tyr Gln Met Ser Asn Leu Ala Ser Gly Val Pro Ser Arg Phe Ser
                85                  90                  95

Ser Ser Gly Ser Gly Thr Asp Phe Thr Leu Thr Ile Ser Ser Leu Gln
            100                 105                 110

Pro Glu Asp Phe Ala Thr Tyr Tyr Cys Ala Gln Asn Leu Glu Ile Pro
        115                 120                 125

Arg Thr Phe Gly Gln Gly Thr Lys Val Glu Leu Lys Arg Ala Thr Pro

-continued

```
                130                 135                 140
Ser His Asn Ser His Gln Val Pro Ser Ala Gly Gly Pro Thr Ala Asn
145                 150                 155                 160

Ser Gly Thr Ser Gly Ser Glu Val Gln Leu Val Gln Ser Gly Pro Gly
                165                 170                 175

Leu Val Gln Pro Gly Gly Ser Val Arg Ile Ser Cys Ala Ala Ser Gly
                180                 185                 190

Tyr Thr Phe Thr Asn Tyr Gly Met Asn Trp Val Lys Gln Ala Pro Gly
                195                 200                 205

Lys Gly Leu Glu Trp Met Gly Trp Ile Asn Thr Tyr Thr Gly Glu Ser
210                 215                 220

Thr Tyr Ala Asp Ser Phe Lys Gly Arg Phe Thr Phe Ser Leu Asp Thr
225                 230                 235                 240

Ser Ala Ser Ala Ala Tyr Leu Gln Ile Asn Ser Leu Arg Ala Glu Asp
                245                 250                 255

Thr Ala Val Tyr Tyr Cys Ala Arg Phe Ala Ile Lys Gly Asp Tyr Trp
                260                 265                 270

Gly Gln Gly Thr Leu Leu Thr Val Ser Ser Glu Phe Gly Gly Ala Pro
                275                 280                 285

Glu Phe Pro Lys Pro Ser Thr Pro Pro Gly Ser Ser Gly Leu Glu Gly
290                 295                 300

Gly Ser Leu Ala Ala Leu Thr Ala His Gln Ala Cys His Leu Pro Leu
305                 310                 315                 320

Glu Thr Phe Thr Arg His Arg Gln Pro Arg Gly Trp Glu Gln Leu Glu
                325                 330                 335

Gln Cys Gly Tyr Pro Val Gln Arg Leu Val Ala Leu Tyr Leu Ala Ala
                340                 345                 350

Arg Leu Ser Trp Asn Gln Val Asp Gln Val Ile Arg Asn Ala Leu Ala
                355                 360                 365

Ser Pro Gly Ser Gly Gly Asp Leu Gly Glu Ala Ile Arg Glu Gln Pro
370                 375                 380

Glu Gln Ala Arg Leu Ala Leu Thr Leu Ala Ala Ala Glu Ser Glu Arg
385                 390                 395                 400

Phe Val Arg Gln Gly Thr Gly Asn Asp Glu Ala Gly Ala Ala Ser Ala
                405                 410                 415

Asp Val Val Ser Leu Thr Cys Pro Val Ala Ala Gly Glu Cys Ala Gly
                420                 425                 430

Pro Ala Asp Ser Gly Asp Ala Leu Leu Glu Arg Asn Tyr Pro Thr Gly
                435                 440                 445

Ala Glu Phe Leu Gly Asp Gly Gly Asp Val Ser Phe Ser Thr Arg Gly
450                 455                 460

Thr Gln Asn Trp Thr Val Glu Arg Leu Leu Gln Ala His Arg Gln Leu
465                 470                 475                 480

Glu Glu Arg Gly Tyr Val Phe Val Gly Tyr His Gly Thr Phe Leu Glu
                485                 490                 495

Ala Ala Gln Ser Ile Val Phe Gly Gly Val Arg Ala Arg Ser Gln Asp
                500                 505                 510

Leu Asp Ala Ile Trp Arg Gly Phe Tyr Ile Ala Gly Asp Pro Ala Leu
                515                 520                 525

Ala Tyr Gly Tyr Ala Gln Asp Gln Glu Pro Asp Ala Arg Gly Arg Ile
530                 535                 540

Arg Asn Gly Ala Leu Leu Arg Val Tyr Val Pro Arg Ser Ser Leu Pro
545                 550                 555                 560
```

```
Gly Phe Tyr Arg Thr Gly Leu Thr Leu Ala Ala Pro Glu Ala Ala Gly
                565                 570                 575

Glu Val Glu Arg Leu Ile Gly His Pro Leu Pro Leu Arg Leu Asp Ala
            580                 585                 590

Ile Thr Gly Pro Glu Glu Gly Gly Arg Leu Glu Thr Ile Leu Gly
            595                 600                 605

Trp Pro Leu Ala Glu Arg Thr Val Val Ile Pro Ser Ala Ile Pro Thr
    610                 615                 620

Asp Pro Arg Asn Val Gly Gly Asp Leu Asp Pro Ser Ser Ile Pro Asp
625                 630                 635                 640

Lys Glu Gln Ala Ile Ser Ala Leu Pro Asp Tyr Ala Ser Gln Pro Gly
                645                 650                 655

Lys Pro Pro His His His His His His Lys Asp Glu Leu
                660                 665

<210> SEQ ID NO 3
<211> LENGTH: 254
<212> TYPE: PRT
<213> ORGANISM: Artificial Sequence
<220> FEATURE:
<223> OTHER INFORMATION: Ep-CAM Binding Protein

<400> SEQUENCE: 3

Asp Ile Gln Met Thr Gln Ser Pro Ser Ser Leu Ser Ala Ser Val Gly
1               5                   10                  15

Asp Arg Val Thr Ile Thr Cys Arg Ser Thr Lys Ser Leu Leu His Ser
            20                  25                  30

Asn Gly Ile Thr Tyr Leu Tyr Trp Tyr Gln Gln Lys Pro Gly Lys Ala
        35                  40                  45

Pro Lys Leu Leu Ile Tyr Gln Met Ser Asn Leu Ala Ser Gly Val Pro
    50                  55                  60

Ser Arg Phe Ser Ser Ser Gly Ser Gly Thr Asp Phe Thr Leu Thr Ile
65                  70                  75                  80

Ser Ser Leu Gln Pro Glu Asp Phe Ala Thr Tyr Tyr Cys Ala Gln Asn
                85                  90                  95

Leu Glu Ile Pro Arg Thr Phe Gly Gln Gly Thr Lys Val Glu Leu Lys
            100                 105                 110

Arg Ala Thr Pro Ser His Asn Ser His Gln Val Pro Ser Ala Gly Gly
        115                 120                 125

Pro Thr Ala Asn Ser Gly Thr Ser Gly Ser Glu Val Gln Leu Val Gln
    130                 135                 140

Ser Gly Pro Gly Leu Val Gln Pro Gly Gly Ser Val Arg Ile Ser Cys
145                 150                 155                 160

Ala Ala Ser Gly Tyr Thr Phe Thr Asn Tyr Gly Met Asn Trp Val Lys
                165                 170                 175

Gln Ala Pro Gly Lys Gly Leu Glu Trp Met Gly Trp Ile Asn Thr Tyr
            180                 185                 190

Thr Gly Glu Ser Thr Tyr Ala Asp Ser Phe Lys Gly Arg Phe Thr Phe
        195                 200                 205

Ser Leu Asp Thr Ser Ala Ser Ala Ala Tyr Leu Gln Ile Asn Ser Leu
    210                 215                 220

Arg Ala Glu Asp Thr Ala Val Tyr Tyr Cys Ala Arg Phe Ala Ile Lys
225                 230                 235                 240

Gly Asp Tyr Trp Gly Gln Gly Thr Leu Leu Thr Val Ser Ser
                245                 250
```

<210> SEQ ID NO 4
<211> LENGTH: 16
<212> TYPE: PRT
<213> ORGANISM: Artificial Sequence
<220> FEATURE:
<223> OTHER INFORMATION: CDR1 (L)

<400> SEQUENCE: 4

Arg Ser Thr Lys Ser Leu Leu His Ser Asn Gly Ile Thr Tyr Leu Tyr
1               5                   10                  15

<210> SEQ ID NO 5
<211> LENGTH: 7
<212> TYPE: PRT
<213> ORGANISM: Artificial Sequence
<220> FEATURE:
<223> OTHER INFORMATION: CDR2 (L)

<400> SEQUENCE: 5

Gln Met Ser Asn Leu Ala Ser
1               5

<210> SEQ ID NO 6
<211> LENGTH: 9
<212> TYPE: PRT
<213> ORGANISM: Artificial Sequence
<220> FEATURE:
<223> OTHER INFORMATION: CDR3 (L)

<400> SEQUENCE: 6

Ala Gln Asn Leu Glu Ile Pro Arg Thr
1               5

<210> SEQ ID NO 7
<211> LENGTH: 5
<212> TYPE: PRT
<213> ORGANISM: Artificial Sequence
<220> FEATURE:
<223> OTHER INFORMATION: CDR1 (H)

<400> SEQUENCE: 7

Asn Tyr Gly Met Asn
1               5

<210> SEQ ID NO 8
<211> LENGTH: 17
<212> TYPE: PRT
<213> ORGANISM: Artificial Sequence
<220> FEATURE:
<223> OTHER INFORMATION: CDR2 (H)

<400> SEQUENCE: 8

Trp Ile Asn Thr Tyr Thr Gly Glu Ser Thr Tyr Ala Asp Ser Phe Lys
1               5                   10                  15

Gly

<210> SEQ ID NO 9
<211> LENGTH: 7
<212> TYPE: PRT
<213> ORGANISM: Artificial Sequence
<220> FEATURE:
<223> OTHER INFORMATION: CDR3 (H)

<400> SEQUENCE: 9

Phe Ala Ile Lys Gly Asp Tyr

-continued

<210> SEQ ID NO 10
<211> LENGTH: 20
<212> TYPE: PRT
<213> ORGANISM: Artificial Sequence
<220> FEATURE:
<223> OTHER INFORMATION: Linker

<400> SEQUENCE: 10

Glu Phe Gly Gly Ala Pro Glu Phe Pro Lys Pro Ser Thr Pro Pro Gly
1               5                   10                  15

Ser Ser Gly Leu
            20

<210> SEQ ID NO 11
<211> LENGTH: 357
<212> TYPE: PRT
<213> ORGANISM: Artificial Sequence
<220> FEATURE:
<223> OTHER INFORMATION: ETA(252-608)

<400> SEQUENCE: 11

Glu Gly Gly Ser Leu Ala Ala Leu Thr Ala His Gln Ala Cys His Leu
1               5                   10                  15

Pro Leu Glu Thr Phe Thr Arg His Arg Gln Pro Arg Gly Trp Glu Gln
            20                  25                  30

Leu Glu Gln Cys Gly Tyr Pro Val Gln Arg Leu Val Ala Leu Tyr Leu
        35                  40                  45

Ala Ala Arg Leu Ser Trp Asn Gln Val Asp Gln Val Ile Arg Asn Ala
    50                  55                  60

Leu Ala Ser Pro Gly Ser Gly Gly Asp Leu Gly Glu Ala Ile Arg Glu
65                  70                  75                  80

Gln Pro Glu Gln Ala Arg Leu Ala Leu Thr Leu Ala Ala Ala Glu Ser
                85                  90                  95

Glu Arg Phe Val Arg Gln Gly Thr Gly Asn Asp Glu Ala Gly Ala Ala
            100                 105                 110

Ser Ala Asp Val Val Ser Leu Thr Cys Pro Val Ala Ala Gly Glu Cys
        115                 120                 125

Ala Gly Pro Ala Asp Ser Gly Asp Ala Leu Leu Glu Arg Asn Tyr Pro
    130                 135                 140

Thr Gly Ala Glu Phe Leu Gly Asp Gly Gly Asp Val Ser Phe Ser Thr
145                 150                 155                 160

Arg Gly Thr Gln Asn Trp Thr Val Glu Arg Leu Leu Gln Ala His Arg
                165                 170                 175

Gln Leu Glu Glu Arg Gly Tyr Val Phe Val Gly Tyr His Gly Thr Phe
            180                 185                 190

Leu Glu Ala Ala Gln Ser Ile Val Phe Gly Gly Val Arg Ala Arg Ser
        195                 200                 205

Gln Asp Leu Asp Ala Ile Trp Arg Gly Phe Tyr Ile Ala Gly Asp Pro
    210                 215                 220

Ala Leu Ala Tyr Gly Tyr Ala Gln Asp Gln Glu Pro Asp Ala Arg Gly
225                 230                 235                 240

Arg Ile Arg Asn Gly Ala Leu Leu Arg Val Tyr Val Pro Arg Ser Ser
                245                 250                 255

Leu Pro Gly Phe Tyr Arg Thr Gly Leu Thr Leu Ala Ala Pro Glu Ala
            260                 265                 270

-continued

```
Ala Gly Glu Val Glu Arg Leu Ile Gly His Pro Leu Pro Leu Arg Leu
            275                 280                 285

Asp Ala Ile Thr Gly Pro Glu Glu Gly Gly Arg Leu Glu Thr Ile
290                 295                 300

Leu Gly Trp Pro Leu Ala Glu Arg Thr Val Val Ile Pro Ser Ala Ile
305                 310                 315                 320

Pro Thr Asp Pro Arg Asn Val Gly Gly Asp Leu Asp Pro Ser Ser Ile
            325                 330                 335

Pro Asp Lys Glu Gln Ala Ile Ser Ala Leu Pro Asp Tyr Ala Ser Gln
            340                 345                 350

Pro Gly Lys Pro Pro
            355
```

<210> SEQ ID NO 12
<211> LENGTH: 113
<212> TYPE: PRT
<213> ORGANISM: Artificial Sequence
<220> FEATURE:
<223> OTHER INFORMATION: VB4-845 light chain variable region

<400> SEQUENCE: 12

```
Asp Ile Gln Met Thr Gln Ser Pro Ser Ser Leu Ser Ala Ser Val Gly
1               5                   10                  15

Asp Arg Val Thr Ile Thr Cys Arg Ser Thr Lys Ser Leu Leu His Ser
            20                  25                  30

Asn Gly Ile Thr Tyr Leu Tyr Trp Tyr Gln Gln Lys Pro Gly Lys Ala
        35                  40                  45

Pro Lys Leu Leu Ile Tyr Gln Met Ser Asn Leu Ala Ser Gly Val Pro
    50                  55                  60

Ser Arg Phe Ser Ser Ser Gly Ser Gly Thr Asp Phe Thr Leu Thr Ile
65                  70                  75                  80

Ser Ser Leu Gln Pro Glu Asp Phe Ala Thr Tyr Tyr Cys Ala Gln Asn
                85                  90                  95

Leu Glu Ile Pro Arg Thr Phe Gly Gln Gly Thr Lys Val Glu Leu Lys
            100                 105                 110

Arg
```

<210> SEQ ID NO 13
<211> LENGTH: 116
<212> TYPE: PRT
<213> ORGANISM: Artificial Sequence
<220> FEATURE:
<223> OTHER INFORMATION: VB4-845 heavy chain variable region

<400> SEQUENCE: 13

```
Glu Val Gln Leu Val Gln Ser Gly Pro Gly Leu Val Gln Pro Gly Gly
1               5                   10                  15

Ser Val Arg Ile Ser Cys Ala Ala Ser Gly Tyr Thr Phe Thr Asn Tyr
            20                  25                  30

Gly Met Asn Trp Val Lys Gln Ala Pro Gly Lys Gly Leu Glu Trp Met
        35                  40                  45

Gly Trp Ile Asn Thr Tyr Thr Gly Glu Ser Thr Tyr Ala Asp Ser Phe
    50                  55                  60

Lys Gly Arg Phe Thr Phe Ser Leu Asp Thr Ser Ala Ser Ala Ala Tyr
65                  70                  75                  80

Leu Gln Ile Asn Ser Leu Arg Ala Glu Asp Thr Ala Val Tyr Tyr Cys
                85                  90                  95
```

```
Ala Arg Phe Ala Ile Lys Gly Asp Tyr Trp Gly Gln Gly Thr Leu Leu
            100                 105                 110
Thr Val Ser Ser
        115

<210> SEQ ID NO 14
<211> LENGTH: 25
<212> TYPE: PRT
<213> ORGANISM: Artificial Sequence
<220> FEATURE:
<223> OTHER INFORMATION: VB4-845 light-heavy chain linker

<400> SEQUENCE: 14

Ala Thr Pro Ser His Asn Ser His Gln Val Pro Ser Ala Gly Gly Pro
1               5                   10                  15

Thr Ala Asn Ser Gly Thr Ser Gly Ser
            20                  25
```

DOSING STRATEGIES FOR TARGETING EPCAM POSITIVE BLADDER CANCER

CROSS REFERENCE TO RELATED APPLICATIONS

This application is the U.S. national stage to PCT/US2016/022085, filed Mar. 11, 2016 which claims priority to U.S. Provisional Application No. 62/132,251 filed Mar. 12, 2015 and U.S. Provisional Application No. 62/267,386 filed Dec. 15, 2015, the contents of each of which is hereby incorporated by reference in its entirety.

DESCRIPTION OF THE TEXT FILE SUBMITTED ELECTRONICALLY

The content of the text file submitted electronically herewith is incorporated herein by reference in its entirety: A computer readable format copy of the Sequence Listing (filename: ELEV_029_02US_SeqList_ST25.txt); date recorded: Sep. 11, 2017; file size 25 KB).

BACKGROUND

Bladder cancer is the $6^{th}$ most common cancer in the United States; it is the $3^{rd}$ most common cancer in men and the $11^{th}$ most common in women. Approximately 75% of bladder cancers are of the non-muscle invasive type (Babjuk et al., 2013). Non-muscle invasive bladder cancers (NMIBCs) are categorized as Ta (non-invasive papillary carcinoma), T1 (tumor invades lamina propria or subepithelial connective tissue), and Tis (carcinoma in situ). Ta tumors are the most common, representing about 70% of NMIBCs, but only about 7% of these are categorized as high-grade (Sylvester et al., 2005). About 20% of NMIBCs are T1 tumors (Anastasiadis et al., 2012) T1 tumors are more aggressive than Ta tumors, and considered high-risk (Babjuk et al., 2013; American Urological Association, 2014) Flat, high-grade tumors confined to the mucosa (non-invasive) are characterized as carcinoma in situ (CIS), ((Babjuk et al., 2013) and these represent approximately 10% of the NMIBCs (Anastasiadis et al., 2012).

The usual first treatment for NMIBC (high grade Ta, T1, and CIS) is transurethral resection of the bladder tumors (TURBT), followed by intravesical immunotherapy, most commonly with *bacillus* Calmette-Guérin (BCG) (Babjuk et al., 2013, American Urological Association 2014), In patients with T1 tumors, a second TURBT is recommended (Babjuk et al., 2013, American Urological Association 2014). Local and systemic side effects are common with intravesical BCG therapy, causing discontinuation of treatment in approximately 20% of patients (Sylvester et al., 2011). Approximately 75% of patients experience local side effects (including cystitis, irritative voiding symptoms, and hematuria), while 40% report systemic side effects, including general malaise and fever (Sylvester et al., 2011). Intravesical BCG failure occurs in up to 40% of patients (Sylvester et al., 2011). Because of the high risk for development of muscle invasive disease, cystectomy is recommended for CIS and high-grade Ta and T1 patients who experience disease recurrence following intravesical therapy. For patients unable or unwilling to undergo cystectomy, treatment options are limited. Thus, there is a need in the art for safe and effective therapies and optimal dosing regimens of safe and effective therapies for bladder cancer.

SUMMARY OF THE INVENTION

In one aspect, the present disclosure provides methods for treating bladder cancer in a subject in need thereof, wherein the methods comprise administering to the subject an immunoconjugate for a first dosing period followed by a second dosing period, wherein the first dosing period comprises administration of the immunoconjugate twice per week, and wherein the second dosing period comprises administration of the immunoconjugate once per week. In some embodiments, the first and second dosing periods are an induction phase of treatment. In some embodiments, the first and second dosing periods are each independently selected from about 4, about 5, about 6, about 7 or about 8 weeks in length. In some embodiments, the first dosing period is a period of at least about 6 consecutive weeks and the second dosing period is a period of at least about 6 consecutive weeks.

In one aspect, the methods further comprise administering the immunoconjugate to the subject for a third dosing period, wherein the immunoconjugate is administered once per week every other week. In some embodiments, the third dosing period is a maintenance phase of treatment. In some aspects, the third dosing period is started in a subject having no histological evidence of high-grade disease following the second dosing period. In other embodiments, the third dosing period is started in a subject that entered the study with low-grade T1 disease and having no evidence of low-grade T1 disease or any high grade disease at the end of the second dosing period. Thus, in some embodiments, a third dosing period or maintenance phase is initiated in a subject in which an event as defined herein has not occurred; and/or in a subject in which complete response as defined herein is achieved following the induction phase of treatment. In some embodiments, the third dosing period begins at least one week or at least two weeks following the end of the second dosing period. In some embodiments, the third dosing period begins no more than 3 weeks following the end of the second dosing period. In some embodiments, the maintenance period is continued for a period of at least about 6 weeks, at least about 8 weeks, at least about 10 weeks, at least about 12 weeks, at least about 14 weeks, at least about 16 weeks, at least about 6 months, at least about 12 months, at least about 18 months, or at least about 24 months. In other embodiments, the maintenance phase is continued until disease recurrence or disease progression.

In one aspect, the methods further comprise removing a bladder tumor prior to the first administration of the immunoconjugate. In some embodiments, the bladder tumor is removed by transurethral resection or fulguration.

In some embodiments, the immunoconjugate comprises a binding protein and a toxin. In further embodiments, the binding protein binds to the extracellular domain of human Ep-CAM. In some embodiments, the immunoconjugate comprises a binding protein that binds to the extracellular binding domain of Ep-CAM, wherein the binding protein is an immunoglobulin binding protein or a non-immunoglobulin polypeptide ligand.

In some embodiments, the immunoglobulin binding protein is an antibody or an antigen-binding fragment thereof. In further embodiments, the binding protein is a monoclonal antibody, Fab, Fab', (Fab')$_2$, single chain fragment (scFv), disulfide-stabilized fragment (dsFv), or a single domain antibody (sdAb). In some embodiments, the antibody or antigen-binding fragment thereof is a murine, chimeric, or humanized antibody or antigen-binding fragment thereof. In particular embodiments, the antibody or antigen-binding fragment thereof is humanized.

In some embodiments, the antibody or antigen-binding fragment thereof comprises a heavy chain CDR1 region having at least about 80%, at least about 85%, at least about 90%, at least about 95%, or at least about 99% homology to the amino acid sequence set forth in SEQ ID NO: 7; a heavy chain CDR2 region having at least about 80%, at least about 85%, at least about 90%, at least about 95%, or at least about 99% homology to the amino acid sequence set forth in SEQ ID NO: 8; and a heavy chain CDR3 region having at least about 80%, at least about 85%, at least about 90%, at least about 95%, or at least about 99% homology to the amino acid sequence set forth in SEQ ID NO: 9. In some embodiments, the antibody or antigen-binding fragment thereof comprises a light chain CDR1 region having at least about 80%, at least about 85%, at least about 90%, at least about 95%, or at least about 99% homology to the amino acid sequence set forth in SEQ ID NO: 4; a light chain CDR2 region having at least about 80%, at least about 85%, at least about 90%, at least about 95%, or at least about 99% homology to the amino acid sequence set forth in SEQ ID NO: 5; and a light chain CDR3 region having at least about 80%, at least about 85%, at least about 90%, at least about 95%, or at least about 99% homology to the amino acid sequence set forth in SEQ ID NO: 6. In some embodiments, the antibody or antigen-binding fragment thereof comprises a heavy chain CDR1, CDR2, and CDR3 consisting of SEQ ID NOs: 7, 8, and 9, respectively; and a light chain CDR1, CDR2, and CDR3 consisting of SEQ ID NOs: 4, 5, and 6, respectively.

In some embodiments, the antibody or antigen-binding fragment thereof comprises a light chain variable region having at least about 80%, at least about 85%, at least about 90%, at least about 95%, or at least about 99% homology to an amino acid sequence as set forth in SEQ ID NO: 12. In some embodiments, the antibody or antigen-binding fragment thereof comprises a heavy chain variable region having at least about 80%, at least about 85%, at least about 90%, at least about 95%, or at least about 99% homology to an amino acid sequence as set forth in SEQ ID NO: 13. In some embodiments, the antibody or antigen-binding fragment thereof comprises an amino acid sequence having at least about 80%, at least about 85%, at least about 90%, at least about 95%, or at least about 99% homology to an amino acid sequence as set forth in SEQ ID NO: 3. Thus, in some embodiments, the antibody or antigen-binding fragment thereof is an scFv that binds to human Ep-CAM, wherein the amino acid sequence of the scFv corresponds to SEQ ID NO: 3. In some embodiments, the antibody or fragment thereof comprises an amino acid sequence having at least 80%, at least 85%, at least 90%, at least 95%, at least 99% or 100% homology to SEQ ID NO: 3 and comprises SEQ ID Nos: 4, 5, 6 and 7, 8, and 9.

In certain embodiments, the immunoconjugates useful in the methods of the present disclosure comprise a toxin. In some embodiments, the toxin is selected from *Pseudomonas* exotoxin A (ETA) or variants thereof, gelonin, bouganin, saporin, ricin, ricin A chain, bryodin, diphtheria toxin, and restrictocin. In some embodiments, the toxin is *Pseudomonas* exotoxin A (ETA) or a variant thereof. In further embodiments, the toxin is ETA(242-608). In some embodiments, the toxin comprises an amino acid sequence having at least about 80%, at least about 85%, at least about 90%, at least about 95%, or at least about 99% homology to SEQ ID NO: 11.

In some embodiments, the immunoconjugates useful in the methods of the present disclosure comprise a binding protein that is attached to a toxin by a peptide linker. Peptide linkers may be cleavable linkers or non-cleavable linkers. In some embodiments, the linker is a cleavable linker selected from the group consisting of a furin sensitive linker, a cathepsin sensitive linker, a metalloproteinase linker, or a lysosomal hydrolase sensitive linker. In some embodiments, the linker is a flexible linker. In some embodiments, the linker is between about 5 and about 50 amino acids in length. In further embodiments, the linker is between about 10 and about 30 amino acids in length. In further embodiments, the linker is about 20 amino acids in length. In some embodiments, the linker has at least about 80%, at least about 85%, at least about 90%, at least about 95%, or at least about 99% homology to SEQ ID NO: 10.

In some embodiments, the immunoconjugates useful in the methods provided herein comprise an amino acid sequence having at least about 80%, at least about 85%, at least about 90%, at least about 95%, or at least about 99% homology to SEQ ID NO: 2. In some embodiments, the immunoconjugates consist of an amino acid sequence as set forth in SEQ ID NO: 2. In some embodiments, the immunoconjugates useful in the methods provided herein comprise an amino acid sequence having at least at least about 80%, at least about 85%, at least about 90%, at least about 95%, or at least about 99% homology to amino acids 23-665 of SEQ ID NO: 2. In some embodiments, the immunoconjugates useful in the methods provided herein consist of an amino acid sequence as set forth as amino acids 23-665 of SEQ ID NO: 2. In some embodiments, the immunoconjugates useful in the methods provided herein comprise an amino acid sequence having at least at least about 80%, at least about 85%, at least about 90%, at least about 95%, or at least about 99% homology to amino acids 23-669 of SEQ ID NO: 2. In some embodiments, the immunoconjugates useful in the methods provided herein consist of an amino acid sequence as set forth as amino acids 23-669 of SEQ ID NO: 2.

In some embodiments, the immunoconjugate is administered to the subject at the same dose level in the first and second dosing periods, such that the subject receives a particular dose of the immunoconjugate twice per week in the first dosing period and the same dose of the immunoconjugate once per week in the second dosing period. In other embodiments, the immunoconjugate is administered to the subject at a higher or lower dose level in the second dosing period relative to the first dosing period. In other embodiments, the immunoconjugate is administered to the subject at the same dose level in the first, second, and third dosing periods, such that the subject receives the same dose of the immunoconjugate twice per week in the first dosing period, once per week in the second dosing period, and once every other week in the third dosing period. In still further embodiments, the immunoconjugate is administered to the subject at different dose levels in the first, second, and/or third dosing periods. In some embodiments, the immunoconjugate is administered to the subject at a dose level of about 5 mg to about 75 mg per dose. In further embodiments, the immunoconjugate is administered to the subject at a dose level of about 10 mg to about 60 mg per dose. In further embodiments, the immunoconjugate is administered to the subject at a dose level of about 20 mg to about 40 mg per dose. In further embodiments, the immunoconjugate is administered to the subject at a dose level of about 30 mg. In some embodiments, the immunoconjugate is administered to the subject at a dose level of 30 mg in the first and second dosing periods. In further embodiments, the immunoconjugate is administered to the subject at a dose level of 30 mg in the first, second, and third dosing periods. In some embodiments, the methods further comprise additional dosing periods in which the dosing level and/or frequency of dosing is further modified.

In some embodiments, the doses of immunoconjugate are administered to the subject at least 48 hours apart. In some embodiments, no more than 2 doses of immunoconjugate are administered to the subject within any 7 day period.

In some embodiments, the immunoconjugate is administered by instillation into the bladder. In further embodiments, the immunoconjugate is administered via a catheter. In some embodiments, the bladder is emptied prior to administration of the immunoconjugate. For example, in some embodiments, the bladder is emptied by the subject by voiding the bladder and/or the bladder is emptied via the catheter prior to administration of the immunoconjugate. In some embodiments, the immunoconjugate is held in the bladder for at least about 15 minutes, at least about 30 minutes, at least about 45 minutes, at least about 1 hour, at least about 1.5 hours, at least about 2 hours, at least about 2.5 hours, at least about 3 hours, or longer. In some embodiments, the subject is positioned in one or more of the following positions during the time the immunoconjugate is in the bladder: upright, prone, supine, and in the left and right lateral decubitus positions. In further embodiments, the subject is position in each of the upright, prone, supine, and left and right lateral decubitus positions during the time the immunoconjugate is in the bladder.

In one aspect, the bladder cancer is non-muscle invasive bladder cancer (NMIBC). In some embodiments, the NMIBC is classified as carcinoma in situ (CIS), Ta, or T1. In some embodiments, the subject has BCG refractive or BCG resistant bladder cancer. In some embodiments, the subject has been previously treated with BCG, interferon, or a combination thereof. In some embodiments, the subject has previously been treated additional intravesicular therapy such as mitomycin, germcitabine, a taxane, interferon, valrubicin or a combination thereof. In some embodiments, the subject failed to respond to previous BCG with or without interferon therapy. In other embodiments, the subject responded to previous BCG with or without interferon therapy but disease subsequently recurred. In some embodiments, the subject has been treated mitomycin, germcitabine, a taxane, interferon, valrubicin or a combination thereof after failure to respond to BCG with or without interferon therapy. In other embodiments, the subject has been treated mitomycin, germcitabine, a taxane, interferon, valrubicin or a combination thereof after a relapse following BCG with or without interferon therapy. In some embodiments, the subject received at least 6, at least 7, at least 8, or at least 9 instillations of BCG. In further embodiments, the at least 6, at least 7, at least 9, or at least 9 instillations of BCG were over 2 cycles of BCG.

In some embodiments, the methods for treating bladder cancer provided herein further comprise administering to the subject at least one additional therapeutic agent. In further embodiments, the additional therapeutic agent is a chemotherapeutic drug or a radiotherapeutic drug. In some embodiments, the chemotherapeutic drugs include, but are not limited to, cisplatin, carboplatin, paclitaxel, docetaxel, 5-fluorouracil, bleomycin, methotrexate, ifosamide, oxaliplatin, cyclophosphamide, dacarbazine, temozolomide, gemcitabine, capecitabine, cladribine, clofarabine, cytarabine, floxuridine, fludarabine, hydroxyurea, pemetrexed, pentostatin, thioguanadine, daunorubicin, doxorubicin, epirubicin, idarubicin, topotecan, irinotecan, etoposide, eniposide, colchicine, vincristine, vinblastine, and vinorelbine. Exemplary cancer specific agents and antibodies include, but are not limited to, Afatinib, Aldesleukin, Alemtuzumab, Axitinib, Belimumab, Bevacizumab, Bortezomib, Bosutinib, Brentuximab vedotin, Cabozantinib, Canakinumab, Carfilzomib, Cetuximab, Crizotinib, Dabrafenib, Dasatinib, Denosumab, Erlotinib, Everolimus, Gefitinib, Ibritumomab tiuxetan, Ibrutinib, Imatinib, Ipilimumab, Lapatinib, Nilotinib, Obinutuzumab, Ofatumumab, Panitumumab, Pazopanib, Pertuzumab, Ponatinib, Regorafenib, Rituximab, Romidepsin, Ruxolitinib, Sipuleucel-T, Sorafenib, Temsirolimus, Tocilizumab, Tofacitinib, Tositumomab, Trametinib, Trastuzumab, Vandetanib, Vemurafenib, Vismodegib, Vorinostat, Ziv-aflibercept, and any combination thereof. In some embodiments, the additional therapeutic agent is administered to the subject prior to, concurrently with, or subsequent to administration of the immunoconjugate. In some embodiments, the additional therapeutic agent is administered systemically. For example, in some embodiments, the additional therapeutic agent is administered by intravenous injection.

Features discussed in relation to the disclosed methods of treating bladder cancer comprising administration of an immunoconjugate are also applicable to the medical use of the immunoconjugate in treating cancer.

In some embodiments, an immunoconjugate for use in treating bladder cancer is provided. In some embodiments, the immunoconjugate comprises binding protein that binds to the extracellular domain of human Ep-Cam and a toxin. In certain embodiments, the use comprises administration of the immunoconjugate at least twice per week for a first dosing period of at least six consecutive weeks, followed by a second dosing period wherein the immunoconjugate is administered once per week for a period of at least six consecutive weeks. In certain embodiments, the use comprises a third dosing period wherein the immunoconjugate is administered once per week every other week. In certain embodiments, the third dosing period is up to 24 months in length or until disease recurrence or disease progression. In certain embodiments, the immunoconjugate is administered to a subject who has undergone transurethral resection to remove a NMBIC tumor from their bladder prior to the first dosing period.

BRIEF DESCRIPTION OF THE DRAWINGS

FIG. 1 is a schematic flow diagram showing steps in a clinical protocol testing a dosing scheme of Vicinium comprising an induction dosing phase and a maintenance dosing phase.

DETAILED DESCRIPTION

Bladder Cancer and EpCAM

The present disclosure provides methods for treatment of bladder cancer comprising administering to a subject in need thereof an immunoconjugate comprising a binding protein specific for Ep-CAM and a toxin, wherein the immunoconjugate is administered in a dosing regimen comprising and induction phase and, optionally, a maintenance phase. In some embodiments, the bladder cancer is non-muscle invasive bladder cancer (NMIBC). Other types of bladder cancer include early stage bladder cancer, non-metastatic bladder cancer, primary bladder cancer, advanced bladder cancer, locally advanced bladder cancer (such as unresectable locally advanced bladder cancer), metastatic bladder cancer, bladder cancer in remission, progressive bladder cancer, or recurrent bladder cancer. In some embodiments, the subject has been diagnosed with bladder cancer or is at risk of developing bladder cancer. In some embodiments, the bladder cancer is NMIBC that is refractory to or intolerant of other treatment options, such as *bacillus* Calmette-Guerin (BCG) treatment or interferon treatment.

Ep-CAM (for Epithelial Cell Adhesion Molecule, which also known as 17-1A, KSA, EGP-2 and GA733-2). Ep-CAM is a transmembrane protein that is highly expressed in many solid tumors, including carcinomas of the bladder, lung, breast, ovary, colorectum, and squamous cell carcinoma of the head and neck, but weakly expressed in most normal epithelial tissues. The role of Ep-CAM in cancer formation remains unclear; however, its expression correlates with the rate of cellular proliferation. Ep-CAM-specific antibodies have been used to image and detect primary tumors and metastases in patients with small cell lung cancer and non-small cell lung cancer. Among anti-Ep-CAM MAbs, PANOREX®, which is a murine monoclonal antibody also known as edrecolomab, had been approved for the treatment of colon cancer in Germany, and is in clinical trials in the United States. Of note, however, PANOREX® treatment has been associated with undesirable side effects, including abdominal cramps, nausea, transient diarrhea and cutaneous urticarial lesions. Clinical trials with other Ep-CAM-targeted antibodies have been less successful; antibody BIS-1 was associated with peripheral vasoconstriction, dyspnea and fever, and antibody 3622W94 was associated with acute necrotizing pancreatitis. The search for an effective, low-toxicity, anti-Ep-CAM antibody continues: a fully humanized anti-Ep-CAM antibody, MT201, purported to act via Antibody-Dependent Cellular Cytotoxicity ("ADCC"), has been reported. A humanized, stabilized, single-chain, anti-Ep-CAM antibody, 4D5MOC-B, which is derived from murine monoclonal antibody MOC31, has also been developed, and is described in International Patent Application No. PCT/EP00/03176, Publication No. WO 00/61635, filed Apr. 10, 2000 and published Oct. 19, 2000, and in Willuda et al. (Cancer Research 59, 5758-5767, 1999). A Phase I dose escalating trial of the Ep-CAM immunoconjugate Vicinium was reported in Kowalski et al. (Drug Des Devel Ther. 2010; 4:313-20 (2012)); and a Phase II study of once-weekly administration of Vicinium was reported in Kowalski et al. (J Urol. 188(5):1712-82012 (2012)).

Ep-CAM Binding Proteins

In one aspect, the present disclosure provides an immunoconjugate comprising a binding protein that binds to Ep-CAM and a toxin. In one embodiment, the binding protein is an antibody or a fragment thereof. Antibodies and fragments thereof are selected from polyclonal antibodies, monoclonal antibodies, Fab, Fab', (Fab')$_2$, single chain fragments (scFv), disulfide-stabilized fragments (dsFv), single domain antibodies (sdAb), diabodies, and cys-diabodies (cysteine-modified diabodies). In some embodiments, diabodies include bivalent, bispecific antibodies or antibody fragments. In some embodiments, diabodies include bivalent antibodies that are made up of the same or different antibody or antibody fragment polypeptides; thus, in some embodiments, the diabodies are homo-multimers or hetero-multimers. Antibodies and fragments thereof may comprise an immunoglobulin constant region selected from the group consisting of IgG1, IgG2, IgG3, IgG4, IgA1, IgA2, IgD, IgE, and IgM. The antibody or fragment thereof may be from any species including mice, rats, rabbits, hamsters, and humans. In one embodiment, the antibody or fragment is chimeric. Chimeric antibodies or fragments thereof are antibody molecules that combine a non-human animal variable region and a constant region or portion of a constant region that is human.

In some embodiments, the antibody or fragment thereof is humanized. As used herein, humanized antibody or humanized antibody fragment means that the antibody or fragment comprises CDRs that are derived from a non-human antibody and framework regions that are derived from a human antibody. The humanization of antibodies from non-human species has been well described in the literature. See for example EP-B1 0 239400 and Carter & Merchant 1997 (Curr Opin Biotechnol 8, 449-454, 1997).

The antigen-binding fragments of any of the above-described monoclonal antibodies, chimeric antibodies or humanized antibodies are prepared using means known in the art, for example, by preparing nested deletions using enzymatic degradation or convenient restriction enzymes. In some embodiments, the humanized antibodies, chimeric antibodies or immunoreactive fragments thereof are screened to ensure that antigen binding has not been disrupted by the humanization, chimerization, or fragmentation of the parent monoclonal antibody. This may be accomplished by any of a variety of means known in the art, including, for example, use of a phage display library.

In one aspect, the binding protein is a non-immunoglobulin polypeptide ligand, such as a protein scaffold. Protein scaffolds are known in the art and comprise proteins or polypeptides that bind to one or more antigens. Such molecules can be designed to bind to a target tumor antigen such as EpCAM, and can be engineered to a desired affinity or avidity or can be designed to tolerate a variety of physical conditions such as extreme pH ranges and high temperatures. Protein scaffolds include, for example, affibodies, adnectins, anticalins, kunitz domain proteins, and other non-immunoglobulin binding proteins known in the art such as, for example, those disclosed in Gebauer and Kerra, *Curr. Opin. Chem. Biol.* 13; 245 (2009).

Toxins

In one aspect, the present disclosure provides an immunoconjugate comprising an antibody fragment that binds to the extracellular domain of human Ep-CAM and a toxin. In some embodiments, the immunotoxin comprises more than one toxin. For example, in some embodiments, the immunoconjugate comprises a diabody comprising more than one toxin.

In some embodiments, the toxin is a molecule that blocks protein synthesis in a target cell, therein leading to cell death. Thus, in some embodiments, the toxin is a cytotoxin. Cytotoxins are known in the art and include, for example, *Pseudomonas* exotoxin A (ETA) or variants thereof; gelonin, bouganin, saporin, ricin, ricin A chain, bryodin, diphtheria toxin, and restrictocin.

In some embodiments, the toxin is a toxic portion of *Pseudomonas* exotoxin A (ETA), or a variant thereof. The toxic portion may comprise one or more *Pseudomonas* exotoxins known in the art. For example, variants of *Pseudomonas* exotoxin, as well as methods of making and using constructs comprising *Pseudomonas* exotoxin and variants, are described in Kreitman, 1995, "Targeting *pseudomonas* exotoxin to hematologic malignancies," Seminars in Cancer Biology 6: 297-306; Pastan, 2003, "Immunotoxins containing *pseudomonas* exotoxin A: a short history," Cancer Immunol. Immunother. 52: 338-341), U.S. Patent Application No. US2003054012; U.S. Pat. Nos. 6,531,133; 6,426,075; 6,423,513; 6,074,644; 5,980,895; 5,912,322; 5,854,044; 5,821,238; 5,705,163; 5,705,156; 5,621,078; 5,602,095; 5,512,658; 5,458,878; 5,082,927; 4,933,288; 4,892,827; 4,677,070; 4,545,985; International Publication Nos. WO98/20135, WO93/25690; WO91/18100; WO91/18099; WO91/09949; and WO88/02401; Kondo et al., 19888, "Activity of immunotoxins constructed with modified *pseudomonas* exotoxin a lacking the cell recognition domain." J Biol Chem. 263:9470-9475; Batra et al., 1989, "Antitumor activity in mice of an immunotoxin made with anti-transferring receptor and a recombinant form of *pseudomonas* exotoxin." Proc Natl. Acad. Sci. USA 86:8545-8549; Puri et al., 1991, "Expression of high-affinity interleukin 4 receptors on murine sarcoma cells and receptor-mediated cytotoxicity of tumor cells to chimeric protein between interleukin 4 and *Pseudomonas* exotoxin." Cancer Res 51:3011-3017; Siegall et al., 1992, "Cytotoxicity of chimeric (human murine) monoclonal antibody BR96 IgG, F(ab')2, and Fab' conjugated to *Pseudomonas* exotoxin." Bioconjug-Chem 3:302-307; Hall et al., 1994, "In vivo efficacy of intrathecal transferrin-*Pseudomonas* exotoxin A immunotoxin against LOX melanoma." Neurosurgery 34:649-655; Kuan and Pai, 1995, "Immunotoxins containing *pseudomonas* exotoxin that target Le y damage human endothelial cells in an antibody-specific mode: relevance to vascular leak syndrome." Clin Cancer Res 1:1589-1594; Kreitman, 1995, "Targeting *pseudomonas* exotoxin to hematologic malignancies." Sem Cancer Biol 6:297-306; Kawooya et al. "The expression, affinity purification and characterization of recombinant *pseudomonas* exotoxin 40 (PE40) secreted from *Escherichia coli*." J Biotechnol 42:9-22; Kaun and Pai, 1995, "Immunotoxins containing *pseudomonas* exotoxin that target LeY damage human endothelial cells in an antibody-specific mode: Relevance to vascular leak syndrome." Clin Cancer Res 1:1589-1594; Puri et al., 1996, "Preclinical development of a recombinant toxin containing circularly permuted interleukin 4 and truncated *Pseudomonas* exotoxin for therapy of malignant astrocytoma." Cancer Res 56:5631-5637; Pai et al., 1996, "Treatment of advanced solid tumors with immunotoxin LMB-1: An antibody linked to *Pseudomonas* exotoxin." Nature Med. 3:350-353; Pai et al., 1998, "Clinical Trials with *pseudomonas* exotoxin immunotoxins." Curr Top. Microbiol. Immunol. 234: 83-96; Klimka et al., 1999, "An anti-CD30 single chain Fv selected by phage display and fused to *pseudomonas* exotoxin A (Ki-4(scFv)-ETA') is a potent immunotoxin against a Hodgkin-derived cell line." British J Cancer 80:1214-1222; Rand et al., 2000, "Intratumoral administration of recombinant circularly permuted interleukin-4-*Pseudomonas* exotoxin in patients with high-grade glioma." Clin Cancer Res 6:2157-2165; Leland et al., 2000, "Human breast carcinoma cells express type II IL-4 receptors and are sensitive to antitumor activity of chimeric IL-4-*pseudomonas* exotoxin fusion protein in vitro and in vivo." Molecular Medicine Today 6:165-178; Tur et al., 2001, "An anti-GD2 single chain Fv selected by phage display and fused to *Pseudomonas* exotoxin A develops specific cytotoxic activity against neuroblastoma derived cell lines." Int J Mol. Med 8:579-584; Onda et al., 2001, "Cytotoxicity of antiosteosarcoma recombinant immunotoxins composed of TP-3 Fv fragments and a truncated *pseudomonas* exotoxin A." J Immunother 24:144-150; 18. "Synergistic interaction between an anti-p185her-2 *pseudomonas* exotoxin fusion protein [scfv(frp5)-eta] and ionizing radiation for inhibiting growth of ovarian cancer cells that overexpress HER-2." Schmidt et al., 2001, "Synergistic interaction between an anti-p185HER-2 *pseudomonas* exotoxin fusion protein [scFv(FRP5)-ETA] and ionizing radiation for inhibiting growth of ovarian cancer cells that overexpress HER-2." Gynecol Oncol 80:145-155; Pastan, 2003, "Immunotoxins containing *pseudomonas* exotoxin A: a short history." Cancer Immunol Immunother 52:338-341; Li et al., 1996, "Crystal structure of the catalytic domain of *Pseudomonas* exotoxin A complexed with a nicotinamide adenine dinucleotide analog: implications for the activation process and for ADP ribosylation." Proc Natl. Acad Sci USA. 9:6902-6906; Kreitman and Pastan, 2003, "Immunobiological treatments of hairy-cell leukaemia." Best Pract Res Clin Haematol. 16:117-33.

In some embodiments, the toxin comprises an ETA variant that, when administered alone, is substantially unable to bind to cells. In some embodiments, the cytotoxic portion comprises ETA(252-608). ETA(252-608), which is a truncated form of ETA that lacks the cell binding domain, is a single polypeptide fusion protein produced by continuous translation of a single construct. In some embodiments, ETA(252-608) comprises an amino acid sequence according to SEQ ID NO: 11.

In other nonlimiting embodiments, the immunoconjugate comprises a binding protein that specifically binds to human EpCAM and a toxin, wherein the toxin comprises an agent that acts to disrupt DNA. Thus, toxins may comprise, without limitation, enediynes (e.g., calicheamicin and esperamicin) and non-enediyne small molecule agents (e.g., bleomycin, methidiumpropyl-EDTA-Fe(II)). Other toxins useful in accordance with the invention include; without limitation, daunorubicin, doxorubicin, distamycin A, cisplatin, mitomycin C, ecteinascidins, duocarmycin/CC-1065, and bleomycin/pepleomycin. In other nonlimiting embodiments, the toxin comprises an agent that acts to disrupt tubulin, Such toxins may comprise, without limitation, rhizoxin/maytansine, paclitaxel, vincristine and vinblastine, colchicine, auristatin dolastatin 10 MMAE, and peloruside A. In other nonlimiting embodiments, the toxin portion of an immunotoxin of the invention may comprise an alkylating agent including, without limitation, Asaley NSC 167780, AZQ NSC 182986, BCNU NSC 409962, Busulfan NSC 750, carboxyphthalatoplatinum NSC 271674, CBDCA NSC 241240, CCNU NSC 79037, CHIP NSC 256927, chlorambucil NSC 3088, chlorozotocin NSC 178248, cis-platinum NSC 119875, clomesone NSC 338947, cyanomorpholinodoxorubicin NSC 357704, cyclodisone NSC 348948, dianhydrogalactitol NSC 132.313, fluorodopan NSC 73754, hepsulfam NSC 329680, hycanthone NSC 142982, melphalan NSC 8806, methyl CCNU NSC 95441, mitomycin C NSC 26980, mitozolamide NSC 353451, nitrogen mustard NSC 762, PCNU NSC 95466, piperazine NSC 344007, piperazinedione NSC 135758, pipobroman NSC 25154, porfiromycin NSC 56410, spirohydantoin mustard NSC 172112, teroxirone NSC 296934, tetraplatin NSC 363812, thio-tepa NSC 6396, triethylenemelamine NSC 9706, uracil nitrogen mustard NSC 34462, and Yoshi-864 NSC 102627. In other nonlimiting embodiments, the toxin portion of an immunotoxin of the invention may comprise an antimitotic agent including, without limitation, allocolchicine NSC 406042, Halichondrin B NSC 609395, colchicine NSC 757, colchicine derivative NSC 33410, dolastatin 10 NSC 376128 (NG-auristatin derived), maytansine NSC 153858, rhizoxin NSC 332598, taxol NSC 125973, taxol derivative NSC 608832, thiocolchicine NSC 361792, trityl cysteine NSC 83265, vinblastine sulfate NSC 49842, and vincristine sulfate NSC 67574

In other nonlimiting embodiments, the toxin portion of an immunotoxin of the invention may comprise an topoisomerase I inhibitor including, without limitation, camptothecin NSC 94600, camptothecin, Na salt NSC 100880, aminocamptothecin NSC 603071, camptothecin derivative NSC 95382, camptothecin derivative NSC 107124, camptothecin derivative NSC 643833, camptothecin derivative NSC 629971, camptothecin derivative NSC 295500, camptothecin derivative NSC 249910, camptothecin derivative NSC 606985, camptothecin derivative NSC 374028, camptothecin derivative NSC 176323, camptothecin derivative NSC 295501, camptothecin derivative NSC 606172, camptothecin derivative NSC 606173, camptothecin derivative NSC 610458, camptothecin derivative NSC 618939, camptothecin derivative NSC 610457, camptothecin derivative NSC 610459, camptothecin derivative NSC 606499, camptothecin derivative NSC 610456, camptothecin derivative NSC 364830, camptothecin derivative NSC 606497, and morpholinodoxorubicin NSC 354646

In other nonlimiting embodiments, the toxin portion of an immunotoxin of the invention may comprise an topoisomerase II inhibitor including, without limitation, doxorubicin NSC 123127, amonafide NSC 308847, m-AMSA NSC 249992, anthrapyrazole derivative NSC 355644, pyrazoloacridine NSC 366140, bisantrene HCL NSC 337766, daunorubicin NSC 82151, deoxydoxorubicin NSC 267469, mitoxantrone NSC 301739, menogaril NSC 269148, N,N-dibenzyl daunomycin NSC 268242, oxanthrazole NSC 349174, rubidazone NSC 164011, VM-26 NSC 122819, and VP-16 NSC 141540.

In other nonlimiting embodiments, the toxin portion of an immunotoxin of the invention may comprise an RNA or DNA antimetabolite including, without limitation, L-alanosine NSC 153353, 5-azacytidine NSC 102816, 5-fluorouracil NSC 19893, acivicin NSC 163501, aminopterin derivative NSC 132483, aminopterin derivative NSC 184692, aminopterin derivative NSC 134033, an antifol NSC 633713, an antifol NSC 623017, Baker's soluble antifol NSC 139105, dichlorallyl lawsone NSC 126771, brequinar NSC 368390, florafur (pro-drug) NSC 148958, 5,6-dihydro-5-azacytidine NSC 264880, methotrexate NSC 740, methotrexate derivative NSC 174121, N-(phosphonoacetyl)-L-aspartate (PALA) NSC 224131, pyrazofurin NSC 143095, trimetrexate NSC 352122, 3-HP NSC 95678, 2'-deoxy-5-fluorouridine NSC 27640, 5-HP NSC 107392, alpha-TGDR NSC 71851, aphidicolin glycinate NSC 303812, ara-C NSC 63878, 5-aza-2'-deoxycytidine NSC 127716, beta-TGDR NSC 71261, cyclocytidine NSC 145668, guanazole NSC 1895, hydroxyurea NSC 32065, inosine glycodialdehyde NSC 118994, macbecin II NSC 330500, pyrazoloimidazole NSC 51143, thioguanine NSC 752, and thiopurine NSC 755.

Furthermore, a toxin may be altered to decrease or inhibit binding outside of the context of the immunoconjugate, or to reduce specific types of toxicity. For example, the toxin may be altered to adjust the isoelectric point to approximately 7.0 such that liver toxicity is reduced.

Linkers

The immunoconjugates useful in the present invention may comprise linkers, such as peptide linkers. For example, in some embodiments, the immunoconjugate comprises an Ep-CAM binding protein linked to a toxin molecule via a peptide linker. Peptide linkers may be cleavable linkers or non-cleavable linkers. Cleavable peptide linkers are known in the art and include, but are not limited to, furin sensitive linkers, cathepsin sensitive linkers, metalloproteinase linkers, and lysosomal hydrolase sensitive linkers. In some embodiments, the linker is a flexible linker. Peptide linkers may be about 5, 6, 7, 8, 9, 10, 11, 12, 13, 14, 15, 16, 17, 18, 19, 20, 21, 22, 23, 24, 25, 26, 27, 28, 29, 30, or more amino acids long. In certain embodiments, the present disclosure provides methods for treating bladder cancer comprising administering to a subject in need thereof an immunoconjugate comprising a binding protein that specifically binds to Ep-CAM, a toxin molecule, and a peptide linker linking the binding protein to the toxin molecule.

VB4-845

In one aspect of the present disclosure, the immunoconjugate is Vicinium. Vicinium contains the active pharmaceutical ingredient VB4-845, which is a recombinant fusion protein produced in *Escherichia coli* (*E. coli*) that expresses a humanized single-chain antibody fragment (scFv) specific for the epithelial cell adhesion molecule (EpCAM) antigen linked to ETA(252-608). VB4-845 is disclosed in U.S. Pat. No. 8,545,840, which is incorporated herein by reference in its entirety. Sequences for VB4-845 are provided below in Table 1.

TABLE 1

VB4-845 sequences

| Description | Sequence | SEQ ID NO |
|---|---|---|
| VB4-845 immuno-conjugate | MKYLLPTAAAGLLLLAAQPAMAHHHHHHDIQMTQSPSSLSASVGD RVTITCRSTKSLLHSNGITYLYWYQQKPGKAPKLLIYQMSNLASG VPSRFSSSGSGTDFTLTISSLQPEDFATYYCAQNLEIPRTFGQGT KVELKRATPSHNSHQVPSAGGPTANSGTSGSEVQLVQSGPGLVQP GGSVRISCAASGYTFTNYGMNWVKQAPGKGLEWMGWINTYTGEST YADSFKGRFTFSLDTSASAAYLQINSLRAEDTAVYYCARFAIKGD YWGQGTLLTVSSEFGGAPEFPKPSTPPGSSGLEGGSLAALTAHQA CHLPLETFTRHRQPRGWEQLEQCGYPVQRLVALYLAARLSWNQVD QVIRNALASPGSGGDLGEAIREQPEQARLALTLAAAESERFVRQG TGNDEAGAASADVVSLTCPVAAGECAGPADSGDALLERNYPTGAE FLGDGGDVSFSTRGTQNWTVERLLQAHRQLEERGYVFVGYHGTFL EAAQSIVFGGVRARSQDLDAIWRGFYIAGDPALAYGYAQDQEPDA RGRIRNGALLRVYVPRSSLPGFYRTGLTLAAPEAAGEVERLIGHP LPLRLDAITGPEEEGGRLETILGWPLAERTVVIPSAIPTDPRNVG GDLDPSSIPDKEQAISALPDYASQPGKPPHHHHHHKDEL | 2 |
| Ep-CAM scFv | DIQMTQSPSSLSASVGDRVTITCRSTKSLLHSNGITYLYWYQQKP GKAPKLLIYQMSNLASGVPSRFSSSGSGTDFTLTISSLQPEDFAT YYCAQNLEIPRTFGQGTKVELKRATPSHNSHQVPSAGGPTANSGT SGSEVQLVQSGPGLVQPGGSVRISCAASGYTFTNYGMNWVKQAPG KGLEWMGWINTYTGESTYADSFKGRFTFSLDTSASAAYLQINSLR AEDTAVYYCARFAIKGDYWGQGTLLTVSS | 3 |
| VB4-845 LCDR1 | RSTKSLLHSNGITYLY | 4 |

TABLE 1-continued

VB4-845 sequences

| Description | Sequence | SEQ ID NO |
|---|---|---|
| VB4-845 LCDR2 | QMSNLAS | 5 |
| VB4-845 LCDR3 | AQNLEIPRT | 6 |
| VB4-845 HCDR1 | NYGMN | 7 |
| VB4-845 HCDR2 | WINTYTGESTYADSFKG | 8 |
| VB4-845 HCDR3 | FAIKGDY | 9 |
| VB4-845 scFv-toxin Linker | EFGGAPEFPKPSTPPGSSGL | 10 |
| ETA (252-608) | EGGSLAALTAHQACHLPLETFTRHRQPRGWEQLEQCGYPVQRLVA LYLAARLSWNQVDQVIRNALASPGSGGDLGEAIREQPEQARLALT LAAAESERFVRQGTGNDEAGAASADVVSLTCPVAAGECAGPADSG DALLERNYPTGAEFLGDGGDVSFSTRGTQNWTVERLLQAHRQLEE RGYVFVGYHGTFLEAAQSIVFGGVRARSQDLDAIWRGFYIAGDPA LAYGYAQDQEPDARGRIRNGALLRVYVPRSSLPGFYRTGLTLAAP EAAGEVERLIGHPLPLRLDAITGPEEEGGRLETILGWPLAERTVV IPSAIPTDPRNVGGDLDPSSIPDKEQAISALPDYASQPGKPP | 11 |
| VB4-84.5 light chain variable region | DIQMTQSPSSLSASVGDRVTITCRSTKSLLHSNGITYLYWYQQKP GKAPKLLIYQMSNLASGVPSRFSSSGSGTDFTLTISSLQPEDFAT YYCAQNLEIPRTFGQGTKVELKR | 12 |
| VB4-845 heavy chain variable region | EVQLVQSGPGLVQPGGSVRISCAASGYTFTNYGMNWVKQAPGKGL EWMGWINTYTGESTYADSFKGRFTFSLDTSASAAYLQINSLRAED TAVYYCARFAIKGDYWGQGTLLTVSS | 13 |
| VB4-845 light-heavy chain linker | ATPSHNSHQVPSAGGPTANSGTSGS | 14 |

In one aspect, the mechanism of action of Vicinium is dependent upon the 2 components of VB4-845. Once bound to the EpCAM antigen on the surface of carcinoma cells, VB4-845 is internalized through an endocytic pathway. Furin contained within the endosomal compartment cleaves a proteolytic site on the surface of ETA(252-608), releasing ETA(252-608). The ETA(252-608) induces cell death by irreversibly blocking protein synthesis through adenosine diphosphate (ADP)-ribosylation of a post-translationally modified histidine residue of elongation factor-2 (EF-2), called diphthamide (Oppenheimer et al., 1981). The truncated version of ETA, ETA(252-608), has been engineered to retain the active domains necessary to induce cell death, but the cell binding domain has been eliminated thereby preventing the ETA(252-608) moiety from entering the cell in the absence of some alternate vehicle, such as via antibody-mediated internalization. Binding to EpCAM must occur to result in ETA(252-608)-mediated effects.

The ETA(252-608) component of the Vicinium fusion protein can cause an immunogenic response when administered systemically to humans. In one aspect, Vicinium is administered in a locally targeted manner in order to limit its systemic exposure and to maximize the concentration of the drug in its target cells. For example, in some embodiments, Vicinium is administered via bladder instillation. In further embodiments, Vicinium is administered into an empty bladder via catheterization. In some embodiments, by administration via instillation, the probability of systemic exposure and subsequent generation of neutralizing antibodies is decreased. Furthermore, in some embodiments, the high local concentrations of Vicinium maximize the likelihood of achieving a therapeutic benefit.

Preclinical study data have shown that Vicinium exhibits potent activity [inhibitory concentration 50% ($IC_{50}$)=0.001-10 pM] against numerous EpCAM-positive cell lines, with selectivity for EpCAM-expressing tumors. In vivo pharmacology demonstrated that Vicinium effectively inhibits tumor growth in several human xenograft animal models. Studies in rats found that the toxicological effects of Vicinium occur at doses 1,000-fold greater than the $IC_{50}$ for activity on tumor cells, with a safety margin of at least 5- to 100-fold.

The present disclosure, in one aspect, provides an improved dosing regimen for Vicinium in non muscle invasive bladder cancer subjects. The dosing regimen comprises an induction phase period comprising 6 weeks of twice-per-week dosing followed by 6 weeks of once per week dosing with Vicinium. In one embodiment, following the induction phase is a maintenance phase. In some embodiments, the maintenance phase comprises at least 1, at least 2, at least 3, at least 6, at least 8, at least 10, at least 12, at least 18, at least 24, at least 36, at least 48, at least 60, at least 72, at least 84, or at least 90 weeks of dosing with Vicinium once every other week. In some embodiments, the maintenance phase comprises up to 91 weeks of dosing with Vicinium. In one aspect, the dosing regimen disclosed herein provides an improved therapeutic result, for example, by preventing disease recurrence.

Definitions

As used herein, the term "animal" includes all members of the animal kingdom, including humans. As used herein, the term "subject" or "patient" refers to any member of the subphylum cordata, including, without limitation, humans and other primates, including non-human primates such as chimpanzees and other apes and monkey species. The terms "mammals" and "animals" are included in this definition. In particular embodiments, the term "subject" as used herein refers to a human that has been diagnosed with bladder cancer, e.g., non muscle-invasive bladder cancer.

As used herein, the phrase "effective amount" is used interchangeably with "therapeutically effective amount" or "therapeutically effective dose" and the like, and means an amount of a therapeutic agent that is effective for treating cancer. As used herein, the phrase "treating cancer" refers to inhibition of cancer cell proliferation, inhibition of cancer spread (metastasis), inhibition of tumor growth, reduction of cancer cell number or tumor growth, decrease in the malignant grade of a cancer (e.g., increased differentiation), or improved cancer-related symptoms. Effective amounts of an immunotoxin as provided herein may vary according to factors such as the disease state, age, sex, weight of the animal.

As used herein, the term "induction phase" refers to an initial course of therapy with the immunoconjugates provided herein. The induction phase for the immunoconjugates provided herein comprises a first dosing period of a twice per week dosing regimen and a second dosing period of a once per week dosing regimen.

As used herein, the term "maintenance phase" refers to a dosing period that follows an induction phase of therapy. Thus, as described herein, the maintenance phase is initiated in a subject following the second dosing period of the induction phase. The maintenance phase for the immunoconjugates provided herein comprises a dosing regimen of once every other week. In some embodiments, the maintenance phase is initiated in subjects who exhibit a complete response to the induction phase of therapy. As used herein, the term "complete response" refers to the response to a therapy in a subject. For example, a subject who exhibits no histological evidence of high-grade disease following the induction phase has exhibited a complete response to the induction phase. In some embodiments, a subject who has exhibited a complete response to the induction phase enters the maintenance phase. Subjects with histologically confirmed evidence of high-grade disease following the induction phase will not enter the maintenance phase. Subjects that enter the study with low grade T1 disease and do not experience a recurrence of T1 disease or have evidence of high-grade disease following the induction phase enter the maintenance phase. Maintenance therapy continues until disease recurrence (i.e., the subject recurs with histologically-confirmed CIS or high-grade papillary Ta or T1 disease, or low-grade T1 if that was the baseline disease) or disease progression (histologically-confirmed disease stage ≥T2), cystectomy, 24 months from start of study, or death, whichever comes first. A subject with disease recurrence or progression will be withdrawn from the study. A subject who relapses with low-grade papillary disease will be allowed to continue maintenance therapy following tumor removal unless the subject had low-grade T1 disease and relapses with low-grade T1 disease.

In some embodiments, the bladder cancer is non-muscle invasive bladder cancer (NMIBC), and subjects subjected to the methods provided herein exhibit event-free survival following the first dose of the immunoconjugate. "Event-free survival" as used herein refers to the interval from the date of first dose of an immunoconjugate provided herein to an event. An "event" herein is defined as high-grade disease, high-grade disease tumor recurrence, tumor progression to muscle invasive bladder cancer, cystectomy for any reason, low grade T1 disease that occurs in a subject that entered the study with low-grade T1 disease, or death.

In some embodiments, the bladder cancer is NMIBC that is classified as carcinoma in situ (CIS), and subjects subjected to the methods provided herein exhibit a complete response following administration of the immunoconjugate. As used herein, "complete response" is defined as one of the following a) normal cystoscopy and non-positive or non-suspicious urine cytology or an abnormal cystoscopy but negative biopsy(ies) (or biopsy(ies) revealing only low-grade disease) and a non-positive or non-suspicious urine; b) negative biopsy (or biopsy revealing only low-grade disease) and non-positive repeat urine cytology; or c) cystoscopy or biopsy revealing only low-grade papillary disease that may be managed by transurethral resection of bladder tumor (TURBT), and not requiring cystectomy or other chemotherapy The term "no evidence of high-grade disease," as used herein, includes at least one of the following: a) normal cystoscopy and non-positive or non-suspicious urine cytology, or a negative biopsy or a biopsy revealing only low-grade papillary disease; b) negative biopsy (or biopsy revealing only low-grade papillary disease) and non-positive repeat urine cytology; or c) cystoscopy or biopsy revealing only low-grade papillary disease that may be managed by transurethral resection of the bladder tumor (TURBT), and not requiring cystectomy Thus, "high grade disease" may be identified by, for example, a biopsy revealing something greater in severity than low-grade papillary disease.

As used herein, the terms "disease recurrence" or "tumor recurrence" refer to the return of histologically-confirmed CIS or high-grade papillary TA or T1 disease. As used herein, "time to disease recurrence" is defined as the interval from the date of the first documented no histological evidence of high-grade disease to the date of first recurrence of histologically-confirmed high-grade disease. In some embodiments, the time to disease recurrence in a subject that received or is receiving the immunoconjugate provided herein is delayed relative to the time to disease recurrence that would occur in a subject that received other available intravesicular therapy.

As used herein, the term "disease progression" refers to histologically-confirmed disease at a stage at or above T2. As used herein, "time to progression" is defined as the time from the date of first dose of the immunoconjugate to the date of histologically confirmed, invasive disease of stage ≥T2. In some embodiments, the time to disease progression is delayed relative to the time to disease progression that would occur in a subject that received other available intravesicular therapy.

"Progression-free survival" is defined herein as the time from the date of first dose of the immunoconjugate to the earlier of (i) the date of histologically-confirmed, stage ≥T2 invasive disease being determined, or (ii) the date of death. "Overall survival" is defined herein as the time from the date of the first dose of immunoconjugate to death due to any cause.

The terms "VB4-845" and "Vicinium" are used interchangeably herein and refer to an immunotoxin that comprises a) the scFv humanized antibody 4D5MOC-B that is fused to b) a truncated form of *Pseudomonas* exotoxin A that consists of amino acids 252-608. In some embodiments, Vicinium is referred to herein as oportuzumab monatox.

The terms "pharmaceutically acceptable excipient" and "pharmaceutically acceptable carrier" are used interchangeably herein and include any and all solvents, dispersion media, coatings, antibacterial and antifungal agents, isotonic and absorption delaying agents and the like. The use of such media and agents for pharmaceutically active substances is well known in the art. Supplementary active ingredients also can be incorporated into the compositions. The antibodies and antigen-binding fragments thereof provided herein may be administered together with other biologically active agents. See, for example. *Remington: The Science and Practice of Pharmacy*, 1995, Gennaro ed. Pharmaceutically acceptable carriers are in general clinical use and/or have approval by a regulatory agency of the Federal or state government, listing in the United States Pharmacopoeia, or general acceptance by those skilled in the relevant art.

"Failure of BCG therapy," as used herein, is defined as treatment with BCG therapy that does not result in an improved outcome in a subject that was treated with BCG therapy for bladder cancer. In some embodiments, a failure of BCG therapy means having had an inadequate response to at least 9 installations of BCG over two cycles (1 induction course+1 maintenance cycle of at least 3 doses, or 2 full induction courses), or have developed recurrent disease following at least 9 installations of BCG. In other embodiments, failure of BCG therapy means having had an inadequate response to at least 7 installations of BCG over 2 cycles (1 induction course of at least 5 doses+1 maintenance cycle of at least 2 doses, or 2 induction courses). A subject with non muscle invasive bladder cancer whose disease is no longer responding to BCG therapy may be either refractory or early relapsing. In a subject whose high-grade disease is refractory to BCG therapy, evaluable high-grade disease remains after adequate BCG treatment. In a subject whose high-grade disease is early-relapsing following BCG therapy, the subject underwent a complete response after adequate BCG treatment but has had an emergence of high-grade disease subsequent to the complete response within 6 months of the last dose of BCG. A subject with low grade T1 disease in which recurrence of T1 disease occurs is also considered early-relapsing.

As used herein, the term "variant" refers to any pharmaceutically acceptable derivative, analogue, or fragment of an immunotoxin, an antibody or antibody fragment, a toxin (e.g., *Pseudomonas* toxin), or cancer therapeutic described herein. A variant also encompasses one or more components of a multimer, multimers comprising an individual component, multimers comprising multiples of an individual component (e.g., multimers of a reference molecule), a chemical breakdown product, and a biological breakdown product. In particular, non-limiting embodiments, an immunotoxin may be a "variant" relative to a reference immunotoxin by virtue of alteration(s) in the Ep-CAM-binding portion and/or the toxin portion of the reference immunotoxin. For example, a variant immunotoxin may contain multimers of the antibody portion and/or the toxin portion. A variant of the toxin portion of the molecule retains toxicity of at least 10 percent and preferably at least 30 percent in a standard assay used to measure toxicity of a preparation of the reference toxin.

As used herein, the phrase "cancer therapeutic" and the like refers to compounds or treatments that are effective in treating or preventing cancer including, without limitation, chemical agents, other immunotherapeutics, cancer vaccines, anti-angiogenic compounds, certain cytokines, certain hormones, gene therapy, radiotherapy, surgery, and dietary therapy. One or more additional cancer therapeutic agents, including chemotherapeutic drugs and cancer specific antibodies, can be administered in addition to the immunoconjugates provided herein, before, during, or after the immunoconjugate administration. Exemplary therapeutic agents include, but are not limited to, 2,2,2 trichlorotriethylamine, 3-HP, 5,6-dihydro-5-5-azacytidine, 5-aza-2'-deoxycytidine, 5-azacytidine, 5-fluorouracil, 5-HP, 5-propagermanium, 6-azauridine, 6-diazo-5-0x0-L-norleucine, 6-mercaptopurine, 6-thioguanine, abrin, Aceglarone, acivicin, Aclacinomycin, actinomycin, actinomycin D, aldesleukin, Alemtuzumab, allocolchicine, allutamine, alpha-fetoprotein, alpha-TGDR, Altretamine, aminocamptothecin, Aminoglutethimide, aminopterin derivative, amonafide, amsacrine, an antifol, anastrozole, ancitabine, angiogenin antisense oligonucleotide, angiostatin, anthramycin, anthrapyrazole derivative, anti-thrombin, aphidicolin glycinate, ara-C, asparaginase, auristatin, autologous cells or tissues, Avastin, azacitidine, azaserine, aziridine, Axitinib, Belimumab, Bevacizumab, Bortezomib, Bosutinib, Brentuximab vedotin, Cabozantinib, Canakinumab, Carfilzomib, Cetuximab, Crizotinib, Dabrafenib, AZQ, *Bacillus*, Baker's soluble antifol, batimastat, BCG live vaccine, bcl-2 antisense oligonucleotide, BCNU, benzodepa, betamethasone, beta-TGDR, biaomycin, bicalutamide, bisantrene, bleomycin, brequinar, buserelin, Busulfan, cactinomycin, calicheamicin, calusterone, campath-1, camptothecin, camptothecin Na salt, capecitabine, carboplain, Carboplatin, carboquone, carboxyphthalatoplatinum, carcinoembryonic antigen, carmofur, carmustine, carnptothecin derivatives, carubicin, carzinophilin, CBDCA, CCNU, CHIP, Chlorabusin, Chlorambucil, chlormadinone acetate, chlornaphazine, chlorozotocin, chromomycins, cisplatin, cisplatinum, cladribine, clomesone, colchicine, colchicine derivative, collagen 14-amino acid peptide, cortisol, cortisone, cyanomorpholinodoxorubicin, cyclarabine, cyclocytidine, cyclodisone, cyclophosphamide, cyclothosphamide, cytarabine, cytochalasin B, cytosine arabinoside, dacarbazine, daclinomycin, dactinomycin, Dasatinib, daunorubicin, defosfamide, dehydrotestosterone, demecolcine, denopterin, deoxydoxorubicin, dexamethasone, dianhydrogalactitol, diaziquone, dichlorallyl lawsone, diphtheria toxin, distamycin A, Docetaxel, dolastatin 10, doxifluridine, doxorubicin, droloxifene, dromostanolone, Duocarmycin/CC-1065, ecteinascidins, edatrexate, eflomithine, elliptinium acetate, emetine, emitefur, endostatin, enocitabine, epipodophyllotoxin, epirubicin, epitiostanol, erbitux, Erlotinib, esperamicin, estramustine, estrogen, ethidium bromide, etoglucid, etoposide, Fadrozole, Fenretinide, fibronectin 29 kDa N-terminal proteolytic fragment, Fibronectin 40 kDa C-terminal N-terminal proteolytic fragment, florafbr (pro-drug), floxuridine, floxuridine, fludarabine, fluorodopan, flutamide, folinic acid, formestane, fosfestrol, fotemustine, gallium nitrate, Gefitinib, gemcitabine, gemcitibine, gemtuzumab, glucocorticoid, goserelin, gramicidin D, granulocyte monocyte colony stimulating factor, guanazole NSC 1895, Guerin, Halichondrin B, hepsulfam, hexamethylmelamine, hexestrol, human chorionic gonadotropin, hycanthone, hydroxyurea, idarubicin, Ifosamide, Imatinib, improsulfan, inosine glycodialdehyde, interferon, interferon-alpha, interferon-beta, interferon-gamma, interleukin-12, interleukin-15, interleukin-18, interleukin-1, interleukin-2, interleukin-2, interleukin-6, interleukins, Irinotecan, iubidazone, kringle 5, L-alanosine, Lapatinib, L-asparaginase, lauprolide acetate, lentinan, letrozole, leuprolide, leuprolide acetate (LUPRON), levamisole, lidocaine, liposomal dihydroxyanthracindione, lomusline, lomustine, lonidamine, lymphokines, lymphotoxin, LYSODREN, macbecin, macrophage inflammatory protein, m-AMSA, mannomustine, maytansine, mechlorethamine, mechlorethamine oxide hydrochloride, medroxyprogesterone, megestrol acetate, melanocyte lineage proteins, melengestrol, melphalan, menogaril, mepitiostane, mercaptopurine, mesna, methidiumpropyl-EDTA-Fe(I1)), methotrexate, methotrexate derivative, meturedepa, miboplatin, miltefosine, mineral corticoid, mithramycin, mitobronitol, mitoguazone, mitolactol, mitolane, mitomycin C, mitotane, mitoxantrone, mitozolamide, mopidamol, morpholinodoxorubicin, mutated tumor-specific antigens, mycophenolic acid, N-(phosphonoacetyl)-L-aspartate (PALA), N,N-dibenzyl daunomycin, nerve growth factor, Nilotinib, nilutamide, nimustine, nitracine, nitrogen mustard, nogalamycin, nonautologous cells or tissues, novembichin, olivomycins, ontak, Onyx-015, oxaliplatin, oxanthrazole, paclitaxel, PCNU, pegaspergase, pelomside A, pentostatin, peplomycin, perfosfamide, phenamet, phenesterine, picamycin, piperazine, piperazinedione, pipobroman, piposulfan, pirarubicin, piritrexim, platelet derived growth factor, platelet factor-4 7.8 kDa proteolytic fragment, platelet factor-4 13 amino acid peptide, plicamycin, podophyllinic acid 2-ethyl-hydrazide, podophyllotoxin, polyestradiol phosphate, porfimir, porfiromycin, prednimustine, prednisone, procabazine, procaine, progestine, prolactin 16 kDa proteolytic fragment, propranolol, *Pseudomonas* exotoxin, PSK, pteropterin, puromycin, pyrazofurin, pyrazoloacridine, pyrazoloimidazole, Ranimustine, razoxane, retinoid, rhizoxin, rhizoxinimaytansine, ricin A, rituxan, rituximab, riuxlmab, Roquinimex, Serpin (Serine Protease Inhibitor), Sizofican, sobuzoxane, Sorafenib, SPARC, 20-amino acid peptide, Spirogermanium, spirohydantoin mustard, straplozocin, streptonigrin, streptozocin, Sunitinib, Tamoxifen, Taxol, Taxol derivative, tegafur, temozoamide, teniposide, tenuazonic acid, teroxirone, testolactone, tetracaine, tetraplatin, thalidomide, Thiamiprine, thiocolchicine, thioepa, thiopurine, thio-tepa, Thrombospondin 1 19 amino acid peptide, tissue plasminogen activator, Tomudex, topotecan, toremifene, trastuzutmaban, tretinoin, triaziquone, triethylenemelamine, triethylenephosphoramide, triethylenethiophosphoramide, trilostane, trimetrexate, triptorelin, trityl cysteine, trofosfamide, Trontecan, tubercidin, tumor necrosis factor-like cytokine, tumor necrosis factors, Ubenimex, uracil mustard, uracil nitrogen mustard, uredepa, urethan, Vandetanib (ZD6474), VEGF antisense oligonucleotide, vinblastine, vinblastine sulfate, vincristine, vincristine sulfate, vindesine, vinorelbine, VM-26, VP-16, Yoshi-864, Zinostatin, zorubicin, Afatinib, Denosumab, Everolimus, Ibritumomab tiuxetan, Ibrutinib, Imatinib, Ipilimumab, Lapatinib, Nilotinib, Obinutuzumab, Ofatumumab, Panitumumab, Pazopanib, Pertuzumab, Ponatinib, Regorafenib, Romidepsin, Ruxolitinib, Sipuleucel-T, Sorafenib, Temsirolimus, Tocilizumab, Tofacitinib, Tositumomab, Trametinib, Trastuzumab, Vandetanib, Vemurafenib, Vismodegib, Vorinostat, Ziv-aflibercept, and any combination thereof.

Unless defined otherwise, all technical and scientific terms used herein have the same meaning as commonly understood by one of ordinary skill in the art to which the invention belongs. Unless otherwise stated, the practice of the present invention employs conventional molecular biology, cell biology, biochemistry, and immunology techniques that are well known in the art and described, for example, in Methods in Molecular Biology, Humana Press; Molecular Cloning: A Laboratory Manual, second edition (Sambrook et al., 1989), Current Protocols in Immunology (J. E. Coligan et. al., eds., 1991); Immunobiology (C. A. Janeway and P. Travers, 1997); Antibodies (P. Finch, 1997); Antibodies: a practical approach (D. Catty., ed., IRL Press, 1988-1989); Monoclonal antibodies: a practical approach (P. Shepherd and C. Dean, eds., Oxford University Press, 2000); Phage display: a laboratory manual (C. Barbas III et al, Cold Spring Harbor Laboratory Press, 2001); and Using antibodies: a laboratory manual (E. Harlow and D. Lane (Cold Spring Harbor Laboratory Press, 1999). The skilled person will recognize that any methods and materials similar or equivalent to those described herein can be used in the practice or testing of the present invention.

All publications referenced herein are incorporated by reference in their entireties for all purposes. Compositions and methods encompassed in the present disclosure will be further described with respect to the following examples; however, the scope of the invention is not to be limited thereby.

EXAMPLES

Example 1. Clinical Study of the Treatment of Non Muscle Invasive Bladder Cancer with Twice Weekly Dosing Followed by Once Weekly Dosing of Vicinium A study is conducted to assess the efficacy and tolerability of Vicinium therapy for the treatment of non muscle-invasive CIS and/or high-grade papillary disease of the bladder in subjects who have previously failed treatment with BCG.
Endpoints In one aspect, the primary endpoint of the study is event-free survival following 18 months of Vicinium therapy. Event-free survival is defined as the interval from the date of the first dose of the immunoconjugate (Vicinium) to an event. An event is defined as persistent high-grade disease, high-grade tumor recurrence, tumor progression to muscle invasive bladder cancer, cystectomy for any reason, or death. Tumor recurrence or progression is histologically confirmed by bladder biopsy.

In another aspect, the primary endpoint of the study is compete response rate in patients with CIS with or without resected papillary disease following the initiation of Vicinium therapy. A complete response is defined as one of the following: a) normal cystoscopy and non-positive or non-suspicious urine cytology; b) negative biopsy (or biopsy revealing only low-grade disease) and non-positive repeat urine cytology; or c) cystoscopy or biopsy revealing low-grade (Ta) papillary disease that may be managed by transurethral resection of bladder tumor (TURBT), and not requiring cystectomy or other chemotherapy. In subjects who have a complete response, the duration of response will be estimated (Kaplan-Meier Estimate). In this aspect, the secondary endpoints include event-free survival.

The secondary endpoints of the study include i) time to cystectomy (defined as the time from the date of the first dose of the immunoconjugate (Vicinium) to physical removal of the bladder); ii) no evidence of high-grade disease (high grade diseases is determined by direct examination or by histology) after 3, 6, 9, 12, 15, 18, 21, and 24 months of Vicinium therapy; time to disease recurrence; time to progression; progression-free survival rate; overall survival; and safety and tolerability of Vicinium.

No evidence of high-grade disease is defined as one of the following: a) normal cystoscopy and non-positive or non-suspicious urine cytology, or a negative biopsy or a biopsy revealing only low-grade papillary disease; b) negative biopsy (or biopsy revealing only low-grade papillary disease) and non-positive repeat urine cytology; c) negative biopsy (or biopsy revealing only low-grade papillary disease) and positive repeat urine cytology and a finding of transitional cell carcinoma (TCC) in the upper urinary tract; or d) cystoscopy or biopsy revealing only low-grade papillary disease that may be managed by transurethral resection of the bladder tumor (TURBT), and not requiring cystectomy. Time to disease recurrence is defined as the number of weeks from the date of the first documented no histological evidence of high-grade disease to the date of first recurrence of histologically-confirmed high-grade disease. Time to progression is defined as the time from the date of first dose of the immunoconjugate (Vicinium) to the date of histologically confirmed, invasive disease of stage ≥T2. Progression-free survival is defined as the time from the date of first dose of the immunoconjugate (Vicinium) to the date of histologically-confirmed, stage ≥T2 invasive disease being determined, or to the date of death. Overall survival is defined as the time from the date of the first dose of the immunoconjugate (Vicinium) to death due to any cause.

Study Design

The study is an open-label, non-randomized, multicenter, multiple-dose study of Vicinium in subjects with histologically-confirmed non muscle-invasive bladder cancer—carcinoma in situ (CIS), high-grade Ta or any grade T1 papillary disease or CIS plus papillary disease—who failed previous treatment with BCG. The subjects will include subjects who have received at least 7 instillations over 2 cycles (1 induction course of at least 5 doses+1 maintenance cycle of at least 2 doses, or 2 induction courses) of BCG (with or without interferon) and have failed to respond (BCG refractory subjects), or subjects who have recurred after achieving a disease-free status following at least 9 instillations of BCG therapy, as described above (BCG relapsing subjects).

The study design comprises an Induction Phase that is 12 weeks in duration and a Maintenance Phase. The total amount of treatment may be up to 104 weeks including induction and maintenance phase. The study is an outpatient study, though intravesicular dosing is performed in the study clinic. Vicinium will be administered as monotherapy, and efficacy and tolerability/safety will be assessed.

Subjects will receive intravesicular Vicinium instillations twice weekly (BIW) for 6 weeks followed by once weekly for 6 weeks for a total of 18 doses in the Induction Phase. The twice weekly doses are to be administered at least 48 hours apart (and no more than 2 doses may be administered within any 7-day period.) After completion of the Induction Phase, subjects will undergo testing to determine their eligibility to continue in the trial. If there is no histological evidence of high-grade disease, the subject will enter the Maintenance Phase. Subjects who enter the study with low grade T1 disease and have a recurrence of low grade T1 disease will not enter the Maintenance Phase. During the Maintenance Phase, Vicinium is administered once every other week for up to 21 months. Subjects with histologically-confirmed evidence of high-grade disease will be withdrawn from the study as a treatment failure.

A schematic flow diagram of the study is provided in FIG. 1.

The subject will be asked to empty his/her bladder prior to administration of Vicinium. Appropriate study personnel will then insert a catheter, and the catheter will be drained. Vicinium is then instilled into the bladder through the catheter. Subjects will be instructed to hold Vicinium in the bladder for 2 hours. They will also be asked to refrain from fluid intake to reduce urine flow during this period. Subjects will be required to position themselves upright (sitting or standing), supine, prone, and in the left and right lateral decubitus positions, for at least 15 minutes each, in any order. At the end of 2-hour period, the subject will void to empty the bladder or the bladder will be emptied by catheter drainage.

An appropriate local anesthetic and sterile lubricant may be used at the time of catheterization. In addition, a single dose of antibiotic may be given prophylactically at the time of catheterization, at the discretion of the Investigator.

The administration procedures for each dose of Vicinium throughout the study are the same as described above.

Vicinium is administered twice weekly via bladder instillation as described above in Weeks 1-6. Each treatment separated by at least 48 hours (and no more than 2 doses may be administered within any 7-day period.) As an example, while a Monday/Thursday or Tuesday/Friday would be optimal, a Monday/Wednesday or a Tuesday/Thursday dosing schedule could be used. Concomitant medications are recorded prior to dosing. Vital signs and collection of AEs, including SAEs, are conducted prior to dosing and prior to clinic discharge. Following the last dose in Week 6, prior to discharge from the clinic, clinical laboratory assessments are to be performed: blood samples collected for hematology and chemistry, urine sample for urinalysis.

During Weeks 7-11, Vicinium is administered once weekly via bladder instillation, as described above. Concomitant medications are recorded prior to dosing. Vital signs and collection of AEs, including SAEs, are conducted prior to dosing and prior to clinic discharge.

The following assessments are to be performed at Week 12. Urine cytology, concomitant medications, vital signs, and AEs, including SAEs, are to be collected prior to dosing. Following the dose in Week 12 and prior to discharge, the following clinical laboratory assessments are to be performed: vital signs, AEs including SAEs, physical exam, hematology and chemistry, urinalysis, and triplicate ECG (spaced one minute apart) for QTc analysis.

During Weeks 13-16, cystoscopy and biopsies will be performed. Biopsies may be random or direct biopsies. Samples will be collected and graded by a central pathologist to determine a subject's eligibility to continue in the trial. To enter the Maintenance Phase, a subject must have no histological evidence of high-grade disease. Any subject with histological evidence of high-grade disease will be discontinued from the trial as a treatment failure.

Week 14 is the earliest a subject may start Maintenance therapy dosing. Maintenance therapy cannot be initiated until all testing procedures are completed and confirmation of no histological evidence of high-grade disease has been provided by the central pathologist. Week 17 is the latest a subject may start Maintenance therapy.

Subjects who have no histological evidence of high-grade disease after the Induction Phase are eligible to enter the Maintenance Phase. Subjects in the Maintenance Phase will be dosed once every other week. The first Maintenance dose will begin no earlier than Week 14 (i.e., at least 1 week must separate the end of Induction and the start of Maintenance therapy) and no later than Week 17 (i.e., 4 weeks following completion of the Induction Phase).

Maintenance therapy continues until disease recurrence (subject recurs with histologically-confirmed CIS or high-grade papillary Ta or T1 disease) or disease progression (histologically-confirmed disease stage ≥T2) or up to 24 months from start of study. A subject with disease recurrence or progression will be withdrawn from the study. A subject who relapses with low-grade papillary disease will be allowed to continue Maintenance therapy following tumor removal. A period of at least 2 weeks, but no more than 3 weeks, must separate tumor removal and dosing of Vicinium.

A positive cytology without cystoscopic evidence of malignant disease will be evaluated (complete evaluation of the upper urinary tract by an appropriate imaging technique; bilateral ureteral cytologies; blind bladder biopsies; uretheral evaluations and biopsy) and followed as clinically appropriate, at discretion of the Investigator. The subject may remain in the study at the discretion of the Investigator. A subject with a second consecutive positive cytology will be considered as having had an event at the time of the second positive or suspicious but non-diagnostic cytology if subsequent follow-up discovers recurrence of high-grade disease, but that subject may remain in the study at the Investigator's discretion prior to that determination of high-grade disease.

The primary endpoint will be evaluated at Month 17 by directed biopsy. EpCAM determination by immunohistochemistry will be obtained on all positive biopsies. In addition, the following procedures will be completed within 2 weeks of the final study visit: physical exam (including height and weight); triplicate ECG (spaced one minute apart) for QTc analysis; vital signs; concomitant medications; AEs, including SAEs; clinical laboratory sample collection (blood samples for hematology and chemistry and urine samples for urinalysis); cytoscopy; and urine cytology.

The schedule of visits and assessments during the induction phase is provided below in Table 2. The schedule of visits and assessments during the maintenance phase is provided below in Table 3. The term "study drug" refers to Vicinium.

TABLE 2

| | Screening/baseline and induction phase | | | | | |
|---|---|---|---|---|---|---|
| | Assessment | | | | | |
| | Screening and Baseline | | Induction Phase Weeks 1-12 Week | | | Weeks 13-16 |
| | −8 to 0 | −1 to 0 | 1 | 2-6 | 7-11 | 12 | 13-16 |
| Informed consent | X | | | | | | |
| Inclusion/Exclusion Criteria | X | | | | | | |
| TURBT | $X^1$ | | | | | | $X^{11}$ |
| Cystoscopy | $X^2$ | | | | | | X |
| Biopsy (directed) | $X^{2,3}$ | | | | | | X |
| Cytology | X | | | $X^7$ | | $X^9$ | |
| Demographics | X | | | | | | |
| Medical history (including previous anti-tumor therapy) | X | | | | | | |
| Physical examination | X | | | $X^7$ | | $X^{10}$ | |
| Weight and height | | | | $X^7$ | | | |
| Prostatic urethral biopsy (males only) | X | | | | | | |
| Upper tract radiological imaging | $X^4$ | | | | | | |
| Triplicate ECG | $X^5$ | | | | | $X^{10}$ | |
| Vital signs | X | | | $X^8$ | $X^8$ | $X^8$ | $X^8$ |
| Clinical Labs (hematology, chemistry, urinalysis) | | X | | $X^7$ | $X^{10}$ | $X^{10}$ | |
| Anti-Vicinium antibody test | | X | | | | | |
| Serum Vicinium Levels[13] | | X | X | X | X | | |
| Urine pregnancy test | | $X^6$ | | | | | |
| Concomitant medication | X | X | | $X^9$ | $X^9$ | $X^9$ | $X^9$ |
| Adverse events (AEs/SAEs) | X | X | | $X^8$ | $X^8$ | $X^8$ | $X^8$ |
| Drug administration (BIW)[12] | | | X | X | | | |
| Drug administration (once/week) | | | | | | X | X |

[1]Must be performed at least 2 weeks prior to study drug administration; all papillary disease much be completely resected. In subjects with T1 disease, a second TURBT must have been performed in order to qualify for study enrollment.
[2]Must have documented non-muscle invasive urothelial bladder cancer that is histologically confirmed by the protocol-specified, independent central pathology reviewer prior to first dose of study drug.
[3]Random biopsies not required prior to study drug administration.
[4]Not required if performed within 6 months before start of dosing.
[5]Single tracing only at Screening; thereafter, triplicate ECGs are to be performed.
[6]Females of childbearing potential only (defined as meeting at least one of the following criteria: a) has not undergone bilateral salpingo-oophorectomy, tubal ligation and/or hysterectomy; b) is greater than age 50 years and has had at least one menstrual period over the last 24 months).
[7]Evaluation performed pre-dose before first dose in Week 1. Note: Week 1 clinical laboratory assessments only need to be performed if the Baseline laboratory assessments were performed >7 days before the first dose of study medication.
[8]Evaluation performed pre-dose and prior to leaving the clinic.
[9]Evaluation performed pre-dose.
[10]Evaluation performed prior to leaving the clinic after the last dose in Week 6 (for clinical labs only) and Week 12 (clinical labs, physical exam, and ECG).
[11]Performed before the start of Maintenance only in subjects with low-grade papillary disease. A period of at least 2 weeks, but no more than 3 weeks, must separate tumor removal and the start of Vicinium Maintenance therapy.
[12]Twice weekly (BIW) dosing with each dose separated by at least 48 hours (and no more than 2 doses within any 7-day period). As an example, while a Monday/Thursday or Tuesday/Friday would be optimal, a Monday/Wednesday or Tuesday/Thursday dosing schedule could be used.
[13]Levels are to be taken at baseline (pre dose of first instillation) and one hour following the initial instillation, the final of the twice-weekly instillations (scheduled $12^{th}$ instillation), and the final of the once-weekly instillations (scheduled $18^{th}$).

TABLE 3

| | Maintenance Phase | | | | | | |
|---|---|---|---|---|---|---|---|
| | Assessment | | | | | | |
| | | Maintenance Phase (Week 17-104) | | | | | Final Visit |
| | Following Induction Phase Treatment | Weeks 14, 17, 24 | Monthly | Every 3 Months | Every 6 Months | Month 12 | Month 18 | Month 24 (End-of-Study) |
| Earliest week to start Maintenance dosing | | Week 14 | | | | | | |
| Last week to start Maintenance dosing | | Week 17 | | | | | | |
| Cytology | | | | $X^5$ | | | | $X^7$ |
| Cystoscopy | $X^1$ | | | $X^5$ | | | | $X^7$ |
| Biopsy (directed) | $X^{1,2}$ | | | | | | $X^2$ | $X^2$ |
| Physical examination | | | | | $X^4$ | | | $X^7$ |
| Triplicate ECG | | | | | | | | $X^7$ |
| Vital signs | | | $X^3$ | | | | | $X^7$ |
| Weight and height | | | | | | $X^4$ | | $X^7$ |
| Anti-Vicinium antibody test[4] | | Week 24 | | | | | | |
| Clinical Labs (hematology, chemistry, urinalysis) | | | | $X^5$ | | | | $X^7$ |
| TURBT[6] | X | | | X | | | | |
| Concomitant medication | | | $X^4$ | | | | | $X^7$ |
| Adverse events (AEs/SAEs) | | | $X^3$ | | | | | $X^7$ |
| Drug administration (once every other week) | | | X | | | | | |

[1]Performed following completion of the Induction Phase to determine qualification for the Maintenance Phase.
[2]Evaluation performed as soon as possible, but no more than 2 weeks, following dosing.
[3]Evaluation performed pre-dose and prior to leaving the clinic.
[4]Evaluation performed pre-dose.
[5]Evaluation performed 1 week and no more than 2 weeks following dosing.
[6]TURBT only for subjects with low-grade papillary disease. A period of at least 2 weeks, but no more than 3 weeks, must separate tumor removal and the start of Vicinium Maintenance therapy following completion of Induction, or the re-start of Vicinium Maintenance therapy in those subjects who relapse with low-grade papillary disease during Maintenance therapy.
[7]Evaluation performed within 2 weeks of end of-study.

Vicinium and Administration of Vicinium

Subjects will receive Vicinium twice weekly (BIW) for 6 weeks and once weekly for 6 weeks during the Induction Phase, and then enter the Maintenance Phase, if eligible. Only subjects who have no histological evidence of high-grade disease after the Induction Phase are eligible to enter the Maintenance Phase. The treatment regimens for the induction and maintenance phases are provided below in Table 4.

TABLE 4

Treatment regimens

| Study Phase | Treatment Regimen |
|---|---|
| Induction Phase (Weeks 1-12) | One intravesical dose of Vicinium 30 mg in 50 mL of saline instilled twice weekly (BIW) for 6 weeks followed by once weekly for 6 weeks, for a total of 12 weeks. The twice weekly doses are to be administered at least 48 hours apart (and no more than 2 doses may be administered within any 7-day period.) As an example, while a Monday/Thursday or Tuesday/Friday would be optimal, a Monday/Wednesday or a Tuesday/Thursday dosing schedule could be used. There will be a total of 18 doses over the 12-week period of the Induction Phase. |
| Maintenance Phase (up to Week 104) | One intravesical dose of Vicinium 30 mg in 50 mL saline instilled once every other week, for up to 24 months (Week 104) from the start of the Induction Phase. Only subjects who have no histological evidence of high-grade disease after the Induction Phase are eligible to enter the Maintenance Phase. |

TABLE 4-continued

Treatment regimens

| Study Phase | Treatment Regimen |
|---|---|
| | Dosing for the first maintenance cycle will begin as soon as practical following completion of the Induction Phase, within the following timeframe: no earlier than Week 14 (i.e., at least 1 week, must separate the end of Induction and the start of Maintenance therapy) and no later than Week 17. |

To reduce urine flow during the instillation and dwell of Vicinium in the bladder, subjects will be asked to refrain from drinking any liquids beginning 2 hours prior to Vicinium instillation through completion of the 2-hour time period during which drug is held in the bladder. Immediately prior to bladder catheter insertion, subjects will empty their bladder. Appropriate study personnel will then insert a catheter into the bladder, and the catheter will be drained. An appropriate local anesthetic and sterile lubricant may be used at the time of catheterization. In addition, a single dose of an oral antibiotic may be given prophylactically at the time of catheterization, at the discretion of the Investigator. The use of any medications must be recorded on the subject case report form.

Vicinium 30 mg in 50 mL of saline will be instilled into the catheter. Subjects will be instructed to hold Vicinium in the bladder for 2 hours, and asked to refrain from fluid intake to reduce urine flow during this period. Subjects will be required to be upright (sitting or standing), prone, supine, and in the left and right lateral decubitus positions, for at least 15 minutes each, in any order. If physically unable, this should be recorded in the CRF. At the end of 2-hour period, the catheter will be removed and the subject will void to empty the bladder.

In this clinical study, Vicinium will be administered as a monotherapy. Beginning 2 weeks prior to the initial dose of Vicinium and throughout the 24-month study period, no anti-cancer therapies, including hormone therapy, radiation therapy, immunotherapy, vaccine therapy, biological therapy, or gene-based therapies will be permitted. Additionally, no other investigational agent is permitted within 4 weeks before the start of Vicinium and throughout the 24-month study period. Any other medication that is considered necessary for the well being of the subject, and that is not expected to interfere with the evaluation of Vicinium, may be given at the discretion of the Investigator.

In subjects who develop low-grade papillary disease during the Maintenance Phase, Vicinium must be interrupted for a minimum of 2 weeks, but for no more than 3 weeks, following tumor removal before restarting Maintenance therapy. Vicinium administration may be postponed for up to 2 weeks if a subject develops any local Grade 3 Adverse Event as defined using the National Cancer Institute Common Terminology Criteria for Adverse Events (NCI-CT-CAE) version 4.03. Vicinium administration may also be postponed for up to 2 weeks at the discretion of the Investigator for any systemic Grade 3 AE. If during these 2 weeks the symptoms improve to Grade 1 or less, dosing may resume. If after 2 weeks the symptoms do not improve, treatment should not be resumed. However, if the AE is assessed by the Investigator as not related to Vicinium and continued treatment is expected to result in a clinical benefit for the subject, treatment may resume as determined in consultation with the Medical Monitor on a case-by-case basis.

Vicinium™ (oportuzumab monatox) is a clear, colorless solution for intravesical administration. It is provided as a frozen product in a glass vial, and then thawed at room temperature prior to preparation for administration. Cloudiness, a change in color and/or the presence of particulate matter may indicate the product has deteriorated. Vicinium 30 mg in 50 mL of saline will be administered intravesically.

For each dose, 1 vial of Vicinium containing 7 mL of Vicinium at a concentration of 5 mg/mL is to be removed from the freezer and allowed to thaw at room temperature (20-25° C. with excursions to 15-30° C. permitted) for 1 hour±15 minutes in an upright position. If large particles are observed or the solution is cloudy in appearance, the vial will be allowed to stand for a maximum additional time of 30 minutes or until a clear solution is observed, whichever comes first. If particulates are still observed after 30 minutes, a fresh vial of Vicinium will be obtained from the freezer. Vials will not be inverted or shaken or placed on their sides during the thawing process. Vials should not be exposed to direct light or heat sources.

Study Population

To qualify for participation, a subject must meet all of the following Inclusion Criteria at the screening/baseline visit:
1. Histologically-confirmed high-grade non muscle-invasive bladder cancer—CIS, Ta or T1 papillary disease or both. This diagnosis is confirmed by the protocol-specified, independent central pathology reviewer prior to subject enrollment in the trial and the start of study treatment.
2. Documented receipt and failure (i.e., not intolerance) of BCG therapy (with or without interferon) for CIS or high-grade Ta or any grade T1 of the bladder, or BCG-refractory or BCG-resistant disease. Male or non-pregnant, non-lactating female, age 18 years or older at date of consent.
3. Females of childbearing potential and all males with partners of childbearing age are eligible only if they agree to use appropriate contraceptive techniques or abstinence during the 24-month study period. A female of childbearing potential is defined as meeting at least one of the following criteria: a) has not undergone bilateral salpingo-oophorectomy, tubal ligation and/or hysterectomy; b) is greater than age 50 years and has had at least one menstrual period within the last 24 months.
4. Bladder biopsy mapping the location of the tumors and quantifying the affected area of bladder within 8 weeks before Vicinium administration.
5. Life expectancy of at least 4 years.
6. Adequate organ function, as defined by the following criteria:
    a. Serum aspartate aminotransferase (AST) and alanine aminotransferase (ALT) ≤3.0× upper limit of normal (ULN);
    b. Total serum bilirubin ≤1.5×ULN (CTCAE Grade ≤1);
    c. Serum creatinine ≤2.0×ULN; subjects with serum creatinine >1×ULN must also have creatinine clearance ≥50 mL/min;
    d. Hemoglobin ≥8.0 g/dL; subjects receiving therapeutic erythropoietin preparations (i.e., epoetin alfa, darbepoetin alfa) are eligible to enroll;
    e. Absolute neutrophil count ≥1500×10$^9$/L;
    f. Platelets ≥75,000×10$^9$/L.
7. Ability to understand and sign an Independent Ethics Committee- or Institutional Review Board-approved informed consent document indicating that the subject (or legally acceptable representative) has been informed of all pertinent aspects of the trial prior to enrollment and is willing and able to comply with scheduled visits, treatment plan, laboratory tests, and other study procedures.

A subject will not be eligible for participation if any one or more of the following criteria apply.
8. The subject is pregnant or breastfeeding.
9. Evidence of urethral or upper tract transitional cell carcinoma (TCC) by biopsy or upper tract radiological imaging (e.g., intravenous pyelogram, computed tomography urogram, or retrograde pyelogram) or evidence of higher stage disease by pelvic imaging within the past 2 years.
10. Subjects with hydronephrosis, except for those subjects where hydronephrosis has been longstanding (i.e., predates the diagnosis of the CIS, Ta or T1 by more than 2 years) and diagnostic evaluation at Screening shows no evidence of tumor.
11. Any intravesicular or other chemotherapy treatment within 2 weeks or any investigational agent within 4 weeks prior to the initial dose of Vicinium.
12. Current severe urinary tract infection or history of recurrent severe bacterial cystitis.
13. Active, uncontrolled impairment of the urogential, renal, hepatobiliary, cardiovascular, gastrointestinal, neurologic or hematopoietic systems which, in the opinion of the Investigator, would predispose the subject to the development of complications from the administration of intravesical therapy and/or general anesthesia.

14. History of other primary malignancy (other than squamous or basal cell skin cancers) that will require concomitant cancer therapy during the 24 months of the study.
15. A QTc interval of >450 msec for males or >470 msec for females at the Screening ECG. If the finding is due to a correctable cause (e.g., hypokalemia, hypomagnesemia), a repeat ECG upon correction may be performed to determine subject eligibility.
16. Subjects who, in the opinion of the Investigator, cannot tolerate intravesical administration or intravesical surgical manipulation (cystoscopy, biopsy) due to the presence of serious comorbid condition(s) (e.g., uncontrolled cardiac or respiratory disorders).

Assessment of Efficacy

Standard cystoscopy is to be performed. Any subject who underwent fluorescence-guided biopsy for the diagnostic samples used for qualification into the study must continue using this modality for cystoscopy throughout the study. During each cystoscopic assessment, bladder mapping must be performed, including documentation of each tumor location and quantification of the overall area of the bladder affected. Cystoscopies will be performed at the end the Induction Phase and every 3 months during the Maintenance Phase. Cytoscopy should be done at least 1 week, but no more than 2 weeks, after the last dose at each of the above time points. Cystoscopy is also performed at Final Visit, within 2 weeks following last dose of Vicinium administration.

Induction Phase cytology samples will be collected at Week 1 prior to the initial (first) dose of Vicinium and pre-dose of Week 12. Cytology samples are also collected every 3 months during the Maintenance Phase (just prior to the first dose of the month) and at Final Visit (within 2 weeks following last dose of Vicinium administration).

Directed biopsies are required for all subjects after completion of the Induction Phase, at Month 18 during the Maintenance Phase, and at Final Visit. No random biopsies are required but may be obtained during workups of suspicious or positive cytologies without obvious anatomical abnormalities. Biopsies are to be obtained and graded as soon as possible, but no more than 2 weeks, after the last dose at each time point. Biopsies at all other time points will only be obtained if evident or suspicious lesions are seen during cystoscopy or when positive or suspicious cytology is observed in the case of negative cystoscopy.

Directed biopsies should be taken from all areas suspicious for disease, including any area of apparent persistent disease and/or any area of inflammation. A minimum of 2 biopsies should be obtained for each subject at each biopsy time point.

Assessment of Safety/Tolerability

An adverse event (AE) is defined as any untoward medical occurrence in a subject administered a pharmaceutical product and which does not necessarily have to have a causal relationship with this treatment. An AE can, therefore, be any unfavorable and unintended sign (that may include an abnormal laboratory finding), symptom, or disease temporally associated with the use of a medicinal product, whether or not related to the medicinal product. Any worsening of the subject's disease under study or other medical conditions will also be considered an AE, unless it is within the normal range of disease fluctuation for that subject. A laboratory test abnormality constitutes an AE only if it is clinically significant such that it induces clinical signs or symptoms, leads to a new diagnosis that was not present at baseline or worsened during active treatment to Grade 3 or Grade 4 toxicity, or requires therapy. An abnormal laboratory value that constitutes a serious adverse event (SAE) or leads to Vicinium discontinuation must be reported and recorded as an AE. All AEs should be treated appropriately. All AEs regardless of suspected causality, occurring from the time of signed Informed Consent and until 30 days after study discontinuation must be recorded on the Adverse Events CRF (AE CRF) with the following minimum information: type of event, duration (start and end dates), severity, seriousness, causality to Vicinium, action taken, and outcome. All AEs will be assessed using the NCI-CTCAE (version 4.03); where applicable, pre-study conditions will be graded using the same scale. For each episode, the highest severity grade attained should be recorded. Adverse events not included in the NCI-CTCAE are to be recorded. Intensity (mild, moderate, or severe) and relationship to Vicinium (not related, unlikely related, possibly related, probably related, or definitely related) will be graded by the Investigator.

A serious adverse event (SAE) or serious suspected adverse reaction is considered serious if, in the view of either the Investigator or sponsor, it results in any of the following outcomes:

Death;
A life-threatening AE, defined as an AE that, in the view of either the Investigator or the Sponsor, places the patient or subject at immediate risk of death. It does not include an AE or suspected adverse reaction that, had it occurred in a more severe form, might have caused death;
A persistent or significant disability/incapacity or substantial disruption of the ability to conduct normal life functions;
A congenital anomaly/birth defect;
Inpatient hospitalization or prolongation of existing hospitalization. The following will not be considered as a hospitalization:
  Elective or pre-planned hospital stays for conditions that existed prior to informed consent and have not worsened or hospital stays for social reasons.
  Treatment on an emergency outpatient basis for an event not fulfilling any of the definitions of an SAE given above and not resulting in hospital admission. "23-hour" hospitalizations for observation should be discussed with the Medical Monitor to determine appropriateness for SAE reporting.
  Routine treatment or monitoring of the studied indication, not associated with any deterioration in condition.
Important medical events that may not result in death, be life-threatening, or require hospitalization may be considered serious when, based on appropriate medical judgment, they may jeopardize the patient or subject and may require medical or surgical intervention to prevent one of the outcomes listed above.

Laboratory assessments will be performed at Baseline, and at the following times in the Induction Phase: before the first dose in Week 1 (if Baseline assessments were performed >7 days prior to the first dose of Vicinium at Week 1), after the last dose in Week 6, and after the last dose in Week 12. During the Maintenance Phase, laboratory assessments will be performed every 3 months (collected 1 week, but no more than 2 weeks following last dose) and at Final Visit (collected no more than 2 weeks following last dose). The following laboratory assessments will be performed:

Serum chemistry, including total bilirubin, ALT, AST, alkaline phosphatase, albumin, lactate dehydrogenase, BUN, creatinine, glucose, sodium, potassium, calcium, phosphorus Hematology, including Complete Blood Count (CBC) with differential, hemoglobin, hematocrit, and platelets Urinalysis with red blood cell (RBC) and white blood cell (WBC) counts All female subjects of childbearing potential (defined as any female who meets at least one of the following criteria: a) has not undergone bilateral salpingo-oophorectomy, tubal ligation and/or hysterectomy; b) is greater than 50 years and has had at least one menstrual period over the last 24 months) will have a urine pregnancy test at Baseline.

Blood will also be collected for determination of plasma anti-Vicinium at Baseline and 6 months of therapy.

A physical examination must be performed by the Investigator or qualified member of the clinic study staff at Screening and at Week 1 prior to the initial dose of Vicinium in the Induction Phase. Physical examinations are also to be performed after last dose in Induction Phase, every 6 months during the Maintenance Phase, and at EOS (or early withdrawal).

Weight and height will be measured at Week 1 prior to the initial dose of Vicinium in the Induction Phase, at Month 12 prior to first dose of Month 12, and at EOS (or early withdrawal).

Complete physical examinations will be performed at Screening and at EOS. All other examinations will be abbreviated and focused, at the discretion of the Investigator, to assess the subject's clinical status, any changes since the previous visit, and any possible AEs.

A single 12-lead ECG will be performed at Screening to determine subject eligibility. Triplicate ECGs (consisting of three individual ECGs spaced one minute apart) for QTc analysis will be performed after the last dose in Induction Phase prior to discharge from the clinic, and at EOS or early withdrawal (within 2 weeks following last dose of Vicinium administration). The ECG should be initiated after at least 10 minutes of quiet rest in a supine position.

Vital signs (blood pressure, pulse, respirations and temperature) will be measured at the following times: Screening, each Induction Phase dosing visit (before dosing and prior to discharge from the clinic), each Maintenance Phase dosing visit (before dosing and prior to discharge from the clinic), and EOS (or early withdrawal). Each vital sign assessment will consist of 2 measurements. Prior to recording the first measurement, the subject should lie in a supine position for 5 minutes. Prior to recording the second measurement, the subject should stand for 3 minutes.

Statistics

The type I (alpha error) for all hypothesis testing will be set at 0.05, and all statistical tests will be two-sided. All confidence intervals will be two-sided 95% confidence intervals. Data will be summarized by reporting the frequency and percentage of subjects in each category for categorical and ordinal measures, and means, standard deviations (SD), medians, minimum and maximum for continuous measures.

Modified intent-to-treat (mITT) Population: The mITT population includes any subject who receives at least one dose of study medication and has an evaluable baseline assessment of disease (biopsy, cystoscopy, and cytology). The mITT population will be the primary efficacy analysis population.

Safety Population: The safety population includes any subject who receives at least one dose of study medication.

The number and percentage of subjects with CIS with or without papillary disease with a complete response will be summarized separately at each assessment. Ninety-five percent (95%) confidence intervals around the complete response rate will be calculated using the Clopper-Pearson method. For subjects with CIS with or without papillary disease who achieve complete response, the duration of response, defined as the start of the complete response to the first documented case of progression or death, will be estimated using the method of Kaplan-Meier. Any patient who does not experience progression or death will be censored at the last non-missing assessment.

Event-free survival will be estimated using the method of Kaplan-Meier. Subjects who do not experience an event will be censored at the last non-missing assessment. Subjects with persistent disease during the Induction Phase will be treated as having an event at Day 1. The ninety-five percent (95%) confidence interval around the event-free survival rate at 18 months will be presented. The study will be deemed successful if the lower bound of the 95% confidence interval excludes 20%. Analyses of other time-to-event efficacy endpoints (time to cystectomy, time to disease recurrence, time to progression, progression-free survival, and overall survival) will be analyzed in a similar manner.

The number and percentage of subjects with no evidence of high-grade disease will be summarized separately at each assessment. Ninety-five percent (95%) confidence intervals around the no evidence of high-grade disease rate will be calculated using the Clopper-Pearson method.

Subset analyses by pathology at study entry will be performed as determined by final distribution.

Adverse events will be coded using the latest available version of the Medical Dictionary for Regulatory Activities (MedDRA). The NCI-CTCAE 4.03 terms are grouped by MedDRA Primary SOCs. Separate tables and/or listings for will be provided for AEs by maximum intensity, treatment-emergent AEs, relationship to study medication, discontinuation of study medication, and death. Tabulations and listings of values for vital signs and clinical laboratory tests will be presented. The tabulation of clinical laboratory tests will be classified as falling above, below, or within normal range. Follow-up ECG and physical examination data will be summarized in tabular format.

Assuming a nonparametric distribution for event-free survival time and the length of follow-up is 24 months, a sample size of 134 subjects will provide at least 80% power to test the null hypothesis that the event-free survival rate at 18 months is 20% versus the alternative hypothesis that the event-free survival rate at 18 months is ≥30%.

REFERENCES

1. American Urological Association. Guideline for the management of noninvasive bladder cancer: (stages Ta, Ti, Tis): 2007 update. Updated February 2014.
2. Anastasiadis A, de Reijke T M. Best practice in the treatment of nonmuscle invasive bladder cancer. Ther Adv Urol. 2012; 4(1):13-32.
3. Babjuk M, Burger M, Zigeuner R, et al. EAU guidelines on non-muscle-invasive urothelial carcinoma of the bladder: update 2013. Eur Urol. 2013; 64(4):639-53.
4. Bladder cancer treatment (PDQ®). General information about bladder cancer.

5. Kowalski M, Entwistle J, Cizeau J, et al. A phase I study of an intravesically administered immunotoxin targeting EpCAM for the treatment of nonmuscle-invasive bladder cancer in BCG-refractory and BCG-intolerant patients. Drug Des Devel Ther. 2010; 4:313-20.
6. Kowalski M, Guindon J, Brazas L, et al. A phase II study of oportuzumab monatox: an immunotoxin therapy for patients with noninvasive urothelial carcinoma in situ previously treated with *bacillus* Calmette-Gurin. J Urol. 2012; 188(5):1712-8.
7. Oppenhemier N J, Bodley J W. Diptheria toxin. Site and configuration of ADP-ribosylation diphthamide in elongation factor 2. J Biol Chem. 1981; 256(16):8579-81.
8. Sylvester R J, van der Meij den A, Witjes J A, et al. High-grade Ta urothelial carcinoma and carcinoma in situ of the bladder. Urology. 2005; 66(6 Suppl 1):90-107.
9. Sylvester R J. *Bacillus* Calmette-Guerin treatment of non-muscle invasive bladder cancer. Int J Urol. 2011; 18(2):113-20.

What is claimed is:

1. A method of treating bladder cancer in a subject in need thereof comprising administering to the subject an immunoconjugate, wherein the immunoconjugate comprises (i) an scFv set forth in SEQ ID NO: 3 that binds to the extracellular domain of human Ep-CAM and (ii) a truncated exotoxin A set forth in SEQ ID NO: 11;
   wherein the immunoconjugate is administered to the subject twice per week for a first dosing period of at least about six consecutive weeks, followed by a second dosing period wherein the immunoconjugate is administered once per week for a period of at least about six consecutive weeks.

2. The method of claim 1, wherein the immunogconjugate is set forth in SEQ ID NO: 2.

3. The method of claim 1, wherein the immunoconjugate is administered to the subject at a dose level of about 10 mg to about 60 mg per dose.

4. The method of claim 1, wherein the doses of the first dosing period are administered at least 48 hours apart.

5. The method of claim 1, wherein the immunoconjugate is administered by instillation into the bladder, wherein the subject is positioned upright, prone, supine, and in the left and right lateral decubitus positions during the time that the immunoconjugate is in the bladder.

6. The method of claim 5, wherein the immunoconjugate is held in the bladder for 2 hours.

7. The method of claim 5, wherein the subject is positioned upright, prone, supine, and in the left and right lateral decubitus positions for at least 15 minutes per position.

8. The method of claim 1, wherein the bladder cancer is BCG refractive, (ii) the bladder cancer is BCG resistant, or (iii) the subject has previously been treated with BCG and/or interferon.

9. The method of claim 1, wherein the bladder cancer is non-muscle invasive bladder cancer (NMIBC).

10. The method of claim 1, wherein the dosing schedule further comprises administering the immunoconjugate to the subject for a third dosing period, wherein the immunoconjugate is administered once per week every other week during the third dosing period.

11. The method of claim 10, wherein the third dosing period is started in subjects having no histological evidence of high-grade disease following the second dosing period.

12. The method of claim 10, wherein the third dosing period begins at least one week following the end of the second dosing period and no more than 3 weeks following the end of the second dosing period.

13. The method of claim 1, further comprising removing a bladder tumor prior to administration of the immunoconjugate.

14. The method of claim 1, further comprising administering to the subject at least one additional therapeutic agent.

15. The method of claim 14, wherein the additional therapeutic agent is a chemotherapeutic drug or a radiotherapeutic drug.

16. The method of claim 15, wherein the additional therapeutic agent is selected from the group consisting of cisplatin, carboplatin, paclitaxel, docetaxel, 5-fluorouracil, bleomycin, methotrexate, ifosamide, and any combination thereof.

17. The method of claim 16, wherein the additional therapeutic agent is administered to the subject concurrently with the immunoconjugate.

* * * * *